(12) United States Patent
Chao

(10) Patent No.: US 10,966,732 B2
(45) Date of Patent: *Apr. 6, 2021

(54) TIBIAL GUIDES, TOOLS AND TECHNIQUES FOR RESECTING THE TIBIAL PLATEAU

(71) Applicant: ConforMIS, Inc., Billerica, MA (US)

(72) Inventor: Nam T. Chao, Marlborough, MA (US)

(73) Assignee: ConforMIS, Inc., Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/671,571

(22) Filed: Nov. 1, 2019

(65) Prior Publication Data

US 2020/0060692 A1 Feb. 27, 2020

Related U.S. Application Data

(63) Continuation of application No. 15/330,828, filed on Nov. 7, 2016, now abandoned, which is a continuation of application No. 13/865,958, filed on Apr. 18, 2013, now Pat. No. 9,486,226.

(60) Provisional application No. 61/635,270, filed on Apr. 18, 2012.

(51) Int. Cl.
*A61B 17/15* (2006.01)

(52) U.S. Cl.
CPC .................. *A61B 17/157* (2013.01)

(58) Field of Classification Search
CPC ..... A61B 17/157; A61B 17/15; A61B 17/151; A61B 17/152; A61B 17/154; A61B 17/155

See application file for complete search history.

(56) References Cited

U.S. PATENT DOCUMENTS

| | | |
|---|---|---|
| 3,789,832 A | 2/1974 | Damadian |
| 3,869,731 A | 3/1975 | Waugh et al. |
| 4,058,486 A | 11/1977 | Mallozzi et al. |
| 4,474,177 A | 10/1984 | Whiteside |
| 4,502,483 A | 3/1985 | Lacey |
| 4,646,729 A | 3/1987 | Kenna et al. |
| 4,759,350 A | 7/1988 | Dunn et al. |
| 4,841,975 A | 6/1989 | Woolson |
| 5,007,936 A | 4/1991 | Woolson |
| 5,098,383 A | 3/1992 | Hemmy et al. |
| 5,107,824 A | 4/1992 | Rogers et al. |
| 5,129,908 A | 7/1992 | Petersen |
| 5,152,796 A | 10/1992 | Slamin |

(Continued)

FOREIGN PATENT DOCUMENTS

| | | |
|---|---|---|
| CN | 101288597 A | 10/2008 |
| DE | 4434539 C2 | 6/1998 |

(Continued)

OTHER PUBLICATIONS

"Arima, MD et al. "Femoral Rotational Alignment, Based on the Anteroposterior Axis, in Total Knee Arthroplasty in a Valgus Knee," The Journal of Bone and Joint Surgery, Incorporated, vol. 77-A, No. 9, pp. 1331-1334, Sep. 1995".

(Continued)

*Primary Examiner* — Anu Ramana
(74) *Attorney, Agent, or Firm* — Sunstein LLP

(57) ABSTRACT

Various patient-specific tibial guide housings, patient-specific tibial guide boxes, and methods of resecting the tibial plateau are disclosed herein.

16 Claims, 18 Drawing Sheets

(56) References Cited

U.S. PATENT DOCUMENTS

| | | |
|---|---|---|
| 5,171,244 A | 12/1992 | Caspari et al. |
| 5,320,102 A | 6/1994 | Paul et al. |
| 5,365,996 A | 11/1994 | Crook |
| 5,370,692 A | 12/1994 | Fink et al. |
| 5,403,319 A | 4/1995 | Matsen, III et al. |
| 5,413,605 A | 5/1995 | Ashby et al. |
| 5,520,695 A | 5/1996 | Luckman |
| 5,569,260 A | 10/1996 | Petersen |
| 5,682,886 A | 11/1997 | Delp et al. |
| 5,735,277 A | 4/1998 | Schuster |
| 5,768,134 A | 6/1998 | Swaelens et al. |
| 5,776,137 A | 7/1998 | Katz |
| 6,023,495 A | 2/2000 | Adler et al. |
| 6,039,764 A | 3/2000 | Pottenger et al. |
| 6,126,690 A | 10/2000 | Ateshian et al. |
| 6,161,080 A | 12/2000 | Aouni-Ateshian et al. |
| 6,205,411 B1 | 3/2001 | DiGioia, III et al. |
| 6,214,052 B1 | 4/2001 | Burkinshaw |
| 6,459,948 B1 | 10/2002 | Ateshian et al. |
| 6,510,334 B1 | 1/2003 | Schuster et al. |
| 6,554,838 B2 | 4/2003 | McGovern et al. |
| 6,575,980 B1 | 6/2003 | Robie et al. |
| 6,589,281 B2 | 7/2003 | Hyde et al. |
| 6,712,856 B1 | 3/2004 | Carignan et al. |
| 6,770,078 B2 | 8/2004 | Bonutti |
| 6,875,236 B2 | 4/2005 | Reiley |
| 6,932,842 B1 | 8/2005 | Litschko et al. |
| 6,969,393 B2 | 11/2005 | Pinczewski et al. |
| 6,978,188 B1 | 12/2005 | Christensen |
| 6,984,249 B2 | 1/2006 | Keller |
| 7,104,996 B2 | 9/2006 | Bonutti |
| 7,239,908 B1 | 7/2007 | Alexander et al. |
| 7,534,263 B2 | 5/2009 | Burdulis et al. |
| 7,618,451 B2 | 11/2009 | Berez et al. |
| 7,806,896 B1 | 10/2010 | Bonutti |
| 7,881,768 B2 | 2/2011 | Lang et al. |
| 7,974,677 B2 | 7/2011 | Mire et al. |
| 7,981,158 B2 | 7/2011 | Fitz et al. |
| 8,062,302 B2 | 11/2011 | Lang et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,092,462 B2 | 1/2012 | Pinczewski et al. |
| 8,105,330 B2 | 1/2012 | Fitz et al. |
| 8,112,142 B2 | 2/2012 | Alexander et al. |
| 8,122,582 B2 | 2/2012 | Burdulis, Jr. et al. |
| RE43,282 E | 3/2012 | Alexander et al. |
| 8,160,345 B2 | 4/2012 | Pavlovskaia et al. |
| 8,221,430 B2 | 7/2012 | Park et al. |
| 8,282,646 B2 | 10/2012 | Schoenefeld et al. |
| 8,306,601 B2 | 11/2012 | Lang et al. |
| 8,333,723 B2 | 12/2012 | Hunter et al. |
| 8,337,501 B2 | 12/2012 | Fitz et al. |
| 8,337,503 B2 | 12/2012 | Lian |
| 8,343,218 B2 | 1/2013 | Lang et al. |
| 8,352,056 B2 | 1/2013 | Lee et al. |
| 8,357,111 B2 | 1/2013 | Caillouette et al. |
| 8,361,076 B2 | 1/2013 | Roose et al. |
| 8,366,771 B2 | 2/2013 | Burdulis, Jr. et al. |
| 8,369,926 B2 | 2/2013 | Lang et al. |
| 8,377,066 B2 | 2/2013 | Katrana et al. |
| 8,377,068 B2 | 2/2013 | Aker et al. |
| 8,377,073 B2 | 2/2013 | Wasielewski |
| 8,377,129 B2 | 2/2013 | Fitz et al. |
| 8,380,471 B2 | 2/2013 | Iannotti et al. |
| 8,398,646 B2 | 3/2013 | Metzger et al. |
| 8,407,067 B2 | 3/2013 | Uthgenannt et al. |
| 8,425,524 B2 | 4/2013 | Aker et al. |
| 8,457,930 B2 | 6/2013 | Schroeder |
| 8,460,304 B2 | 6/2013 | Fitz et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,529,630 B2 | 9/2013 | Bojarski et al. |
| 8,532,807 B2 | 9/2013 | Metzger |
| 8,551,099 B2 | 10/2013 | Lang et al. |
| 8,551,102 B2 | 10/2013 | Fitz et al. |
| 8,551,103 B2 | 10/2013 | Fitz et al. |
| 8,551,169 B2 | 10/2013 | Fitz et al. |
| 8,556,906 B2 | 10/2013 | Fitz et al. |
| 8,556,907 B2 | 10/2013 | Fitz et al. |
| 8,561,278 B2 | 10/2013 | Fitz et al. |
| 8,562,611 B2 | 10/2013 | Fitz et al. |
| 8,562,618 B2 | 10/2013 | Fitz et al. |
| 8,568,479 B2 | 10/2013 | Fitz et al. |
| 8,568,480 B2 | 10/2013 | Fitz et al. |
| 8,585,708 B2 | 11/2013 | Fitz et al. |
| 8,617,172 B2 | 12/2013 | Fitz et al. |
| 8,623,026 B2 | 1/2014 | Wong et al. |
| 8,634,617 B2 | 1/2014 | Tsougarakis et al. |
| 8,638,998 B2 | 1/2014 | Steines et al. |
| 8,641,716 B2 | 2/2014 | Fitz et al. |
| 8,657,827 B2 | 2/2014 | Lang et al. |
| 8,709,089 B2 | 4/2014 | Lang et al. |
| 8,768,028 B2 | 7/2014 | Lang et al. |
| 8,801,720 B2 | 8/2014 | Park et al. |
| 8,951,259 B2 | 2/2015 | Fitz et al. |
| 8,951,260 B2 | 2/2015 | Lang et al. |
| 8,998,915 B2 | 4/2015 | Fitz et al. |
| 9,023,050 B2 | 5/2015 | Lang et al. |
| 9,055,953 B2 | 6/2015 | Lang et al. |
| 9,066,728 B2 | 6/2015 | Burdulis, Jr. et al. |
| 9,072,531 B2 | 7/2015 | Fitz et al. |
| 9,084,617 B2 | 7/2015 | Lang et al. |
| 9,095,353 B2 | 8/2015 | Burdulis, Jr. et al. |
| 9,107,679 B2 | 8/2015 | Lang et al. |
| 9,107,680 B2 | 8/2015 | Fitz et al. |
| 9,113,921 B2 | 8/2015 | Lang et al. |
| 9,125,672 B2 | 9/2015 | Fitz et al. |
| 9,125,673 B2 | 9/2015 | Fitz et al. |
| 9,186,161 B2 | 11/2015 | Lang et al. |
| 9,216,025 B2 | 12/2015 | Fitz et al. |
| 9,220,516 B2 | 12/2015 | Lang et al. |
| 9,220,517 B2 | 12/2015 | Lang et al. |
| 9,241,724 B2 | 1/2016 | Lang et al. |
| 9,241,725 B2 | 1/2016 | Lang et al. |
| 9,295,481 B2 | 3/2016 | Fitz et al. |
| 9,295,482 B2 | 3/2016 | Fitz et al. |
| 9,308,005 B2 | 4/2016 | Fitz et al. |
| 9,308,053 B2 | 4/2016 | Bojarski et al. |
| 9,314,256 B2 | 4/2016 | Fitz et al. |
| 9,326,780 B2 | 5/2016 | Wong et al. |
| 9,333,085 B2 | 5/2016 | Fitz et al. |
| 9,358,018 B2 | 6/2016 | Fitz et al. |
| 9,375,222 B2 | 6/2016 | Fitz et al. |
| 9,381,025 B2 | 7/2016 | Fitz et al. |
| 9,408,615 B2 | 8/2016 | Fitz et al. |
| 9,486,226 B2 | 11/2016 | Chao et al. |
| 9,579,110 B2 | 2/2017 | Bojarski et al. |
| 9,603,711 B2 | 3/2017 | Bojarski et al. |
| 9,913,723 B2 | 3/2018 | Fitz et al. |
| 2002/0059049 A1 | 5/2002 | Bradbury et al. |
| 2002/0072821 A1 | 6/2002 | Baker |
| 2002/0087274 A1 | 7/2002 | Alexander et al. |
| 2003/0028196 A1 | 2/2003 | Bonutti |
| 2004/0117015 A1 | 6/2004 | Biscup |
| 2004/0236424 A1 | 11/2004 | Berez et al. |
| 2005/0107886 A1 | 5/2005 | Crabtree et al. |
| 2005/0148843 A1 | 7/2005 | Roose et al. |
| 2005/0177169 A1 | 8/2005 | Fisher et al. |
| 2005/0197814 A1 | 9/2005 | Aram et al. |
| 2006/0094951 A1 | 5/2006 | Dean et al. |
| 2006/0149283 A1 | 7/2006 | May et al. |
| 2007/0226986 A1 | 10/2007 | Park et al. |
| 2007/0233141 A1 | 10/2007 | Park et al. |
| 2007/0233156 A1 | 10/2007 | Metzger |
| 2007/0288030 A1 | 12/2007 | Metzger et al. |
| 2008/0021566 A1 | 1/2008 | Peters et al. |
| 2008/0114370 A1 | 5/2008 | Schoenefeld et al. |
| 2008/0140212 A1 | 6/2008 | Metzger et al. |
| 2008/0147072 A1 | 6/2008 | Park et al. |
| 2008/0161815 A1* | 7/2008 | Schoenefeld ...... A61B 17/1764 606/87 |
| 2008/0194997 A1 | 8/2008 | Zhang |

(56) References Cited

U.S. PATENT DOCUMENTS

| | | |
|---|---|---|
| 2008/0257363 A1 | 10/2008 | Schoenefeld et al. |
| 2008/0262624 A1 | 10/2008 | White et al. |
| 2009/0024131 A1 | 1/2009 | Metzger et al. |
| 2009/0087276 A1 | 4/2009 | Rose |
| 2009/0088753 A1 | 4/2009 | Aram et al. |
| 2009/0088758 A1 | 4/2009 | Bennett |
| 2009/0099567 A1 | 4/2009 | Zajac |
| 2009/0110498 A1 | 4/2009 | Park |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0151736 A1 | 6/2009 | Belcher et al. |
| 2009/0163922 A1 | 6/2009 | Meridew et al. |
| 2009/0254093 A1 | 10/2009 | White et al. |
| 2009/0270868 A1 | 10/2009 | Park et al. |
| 2009/0281544 A1* | 11/2009 | Anthony ............ A61B 17/15 606/87 |
| 2010/0042105 A1 | 2/2010 | Park et al. |
| 2010/0049195 A1 | 2/2010 | Park et al. |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0256479 A1 | 10/2010 | Park et al. |
| 2010/0292963 A1 | 11/2010 | Schroeder |
| 2010/0303313 A1 | 12/2010 | Lang et al. |
| 2010/0305573 A1 | 12/2010 | Fitz et al. |
| 2011/0040387 A1 | 2/2011 | Ries et al. |
| 2011/0046735 A1 | 2/2011 | Metzger et al. |
| 2011/0054478 A1 | 3/2011 | Vanasse et al. |
| 2011/0071533 A1 | 3/2011 | Metzger et al. |
| 2011/0092804 A1 | 4/2011 | Schoenefeld et al. |
| 2011/0093108 A1 | 4/2011 | Ashby et al. |
| 2011/0166578 A1 | 7/2011 | Stone et al. |
| 2011/0190899 A1 | 8/2011 | Pierce et al. |
| 2011/0218542 A1 | 9/2011 | Lian |
| 2011/0218545 A1 | 9/2011 | Catanzarite et al. |
| 2012/0089146 A1 | 4/2012 | Ferko et al. |
| 2012/0123422 A1 | 5/2012 | Agnihotri et al. |
| 2012/0141034 A1 | 6/2012 | Iannotti et al. |
| 2012/0151730 A1 | 6/2012 | Fitz et al. |
| 2012/0239045 A1 | 9/2012 | Li |
| 2012/0265496 A1 | 10/2012 | Mahfouz |
| 2012/0316564 A1 | 12/2012 | Serbousek et al. |
| 2012/0323246 A1 | 12/2012 | Catanzarite et al. |
| 2013/0006250 A1 | 1/2013 | Metzger et al. |
| 2013/0006251 A1 | 1/2013 | Aram et al. |
| 2013/0018378 A1 | 1/2013 | Hananouchi et al. |
| 2013/0035766 A1 | 2/2013 | Meridew |
| 2013/0066319 A1 | 3/2013 | Aram et al. |
| 2013/0066321 A1 | 3/2013 | Mannss et al. |
| 2013/0110116 A1 | 5/2013 | Kehres et al. |
| 2013/0119579 A1 | 5/2013 | Iannotti et al. |
| 2013/0138111 A1 | 5/2013 | Aram et al. |
| 2013/0184764 A1 | 7/2013 | Stone et al. |
| 2013/0199259 A1 | 8/2013 | Smith |
| 2014/0018813 A1 | 1/2014 | McKinnon et al. |
| 2014/0025348 A1 | 1/2014 | Abiven |
| 2014/0074441 A1 | 3/2014 | Fitz et al. |
| 2014/0107715 A1 | 4/2014 | Heilman et al. |
| 2014/0180295 A1 | 6/2014 | Buza et al. |
| 2014/0324205 A1 | 10/2014 | Park et al. |
| 2015/0150644 A1 | 6/2015 | Lang et al. |
| 2016/0045317 A1 | 2/2016 | Lang et al. |
| 2016/0074124 A1 | 3/2016 | Fitz et al. |
| 2017/0007414 A1 | 1/2017 | Fitz et al. |
| 2017/0056024 A1 | 3/2017 | Chao |
| 2018/0228614 A1 | 8/2018 | Lang et al. |
| 2018/0235762 A1 | 8/2018 | Radermacher et al. |
| 2018/0263782 A1 | 9/2018 | Lang et al. |
| 2018/0360609 A1 | 12/2018 | Steines et al. |
| 2019/0008532 A1 | 1/2019 | Fitz et al. |
| 2019/0038298 A1 | 2/2019 | Bojarski et al. |
| 2020/0060692 A1 | 2/2020 | Chao |
| 2020/0214843 A1 | 7/2020 | Radermacher et al. |

FOREIGN PATENT DOCUMENTS

| | | |
|---|---|---|
| EP | 0337901 A1 | 10/1989 |
| EP | 0704193 A1 | 4/1996 |
| EP | 0732092 A2 | 9/1996 |
| EP | 0908836 A2 | 4/1999 |
| EP | 1074229 B1 | 10/2005 |
| WO | WO-9325157 A1 | 12/1993 |
| WO | WO-9400056 A1 | 1/1994 |
| WO | WO-9528688 A1 | 10/1995 |
| WO | WO-9832384 A1 | 7/1998 |
| WO | WO-9932045 A1 | 7/1999 |
| WO | WO-0035346 A2 | 6/2000 |
| WO | WO-0047103 A2 | 8/2000 |
| WO | WO-0059411 A1 | 10/2000 |
| WO | WO-0068749 A1 | 11/2000 |
| WO | WO-0166021 A1 | 9/2001 |
| WO | WO-0170142 A1 | 9/2001 |
| WO | WO-0177988 A2 | 10/2001 |
| WO | WO-0222013 A1 | 3/2002 |
| WO | WO-0222014 A1 | 3/2002 |
| WO | WO-03037192 A1 | 5/2003 |
| WO | WO-2004049981 A2 | 6/2004 |
| WO | WO-2008021494 A2 | 2/2008 |
| WO | WO-2008117028 A1 | 10/2008 |
| WO | WO-2009001083 A1 | 12/2008 |
| WO | WO-2009009660 A1 | 1/2009 |
| WO | WO-2009106816 A1 | 9/2009 |
| WO | WO-2010099353 A1 | 9/2010 |
| WO | WO-2010148103 A1 | 12/2010 |
| WO | WO-2011059641 A1 | 5/2011 |
| WO | WO-2011101474 A1 | 8/2011 |
| WO | WO-2011130421 A1 | 10/2011 |
| WO | WO-2012021241 A2 | 2/2012 |
| WO | WO-2012021846 A2 | 2/2012 |
| WO | WO-2012021894 A2 | 2/2012 |
| WO | WO-2012021895 A2 | 2/2012 |
| WO | WO-2012051542 A2 | 4/2012 |
| WO | WO-2012173929 A1 | 12/2012 |
| WO | WO-2013055617 A1 | 4/2013 |
| WO | WO-2013062850 A1 | 5/2013 |
| WO | WO-2013173926 A1 | 11/2013 |
| WO | WO-2014070889 A1 | 5/2014 |
| WO | WO-2014145267 A1 | 9/2014 |
| WO | WO-2015112570 A1 | 7/2015 |

OTHER PUBLICATIONS

"Chao, PhD. et al. "Computer-Aided Preoperative Planning in Knee Osteotomy," The Iowa Orthopaedic Journal, vol. 15, pp. 4-18, 1995".

Chelule et al. "Computer Aided Design of Personalized Jigs in Total Knee Replacement", 3rd Annual Meeting of CAOS Int'l Proc., Spain, Jun. 18, 21, 2003, pp. 58-59.

Chelule et al. "Patient-Specific Template to Preserve Bone Stock in Total Knee Replacement: Preliminary Results", 15th Annual ISTA Symposium, Sep. 2002, 1 page.

Cohen et al. "Computer-Aided Planning of Patellofemoral Joint OA Surgery: Developing Physical Models from Patient MRI", MIC-CAI, Oct. 11-13, 1998, 13 pages.

Cohen et al. "Knee Cartilage Topography Thickness and Contact Areas From MRI: In-Vitro Calibration and In-Vivo Measurements", Osteoarthritis and Cartilage vol. 7, No. 1, pp. 95-109 (1999).

"Decision Denying Institution of Inter Partes Review of U.S. Pat. No. 7,534,263, Case No. IPR2017-00545, entered Jul. 13, 2017, 16 pages".

"Decision Denying Institution of Inter Partes Review of U.S. Pat. No. 8,377,129, Case No. IPR2017-00372, entered Jun. 13, 2017, 20 pages".

"Decision Denying Institution of Inter Partes Review of U.S. Pat. No. 8,657,827, Case Nos. IPR2017-00983 & IPR2017-00984, entered Sep. 12, 2017, 33 pages".

"Decision Denying Institution of Inter Partes Review of U.S. Pat. No. 9,216,025, Case No. IPR2017-00307, entered Jul. 26, 2017, 18 pages".

(56) References Cited

OTHER PUBLICATIONS

"Decision Denying Institution of Inter Partes Review of U.S. Pat. No. 9,295,482, Case Nos. IPR2017-00487 & IPR2017-00488, entered Jul. 7, 2017, 35 pages".
"Decision for Institution of Inter Partes Review of U.S. Pat. No. 9,055,953, Case No. IPR2016-01874, entered Mar. 27, 2017, 24 pages".
"Decision granting Request for Ex Parte Reexamination of U.S. Pat. No. 8,377,129, dated Mar. 30, 2018, 16 pages".
"Decision on Institution of Inter Partes Review of U.S. Pat. No. 7,534,263, Case No. IPR2017-00544, entered Jul. 13, 2017, 37 pages".
"Decision on Institution of Inter Partes Review of U.S. Pat. No. 7,981,158, Case No. IPR2017-00510, entered Jun. 14, 2017, 31 pages".
"Decision on Institution of Inter Partes Review of U.S. Pat. No. 7,981,158, Case No. IPR2017-00511, entered Jun. 14, 2017, 28 pages".
"Decision on Institution of Inter Partes Review of U.S. Pat. No. 8,062,302, Case Nos. IPR2017-00778 & IPR2017-00779 and IPR2017-00780, entered Aug. 7, 2017, 41 pages".
"Decision on Institution of Inter Partes Review of U.S. Pat. No. 8,551,169, Case No. IPR2017-00373, entered Jun. 13, 2017, 20 pages".
"Decision on Institution of Inter Partes Review of U.S. Pat. No. 9,216,025, Case No. IPR2017-00115, entered Apr. 26, 2017, 31 pages".
Delp et al. A Graphics-Based Software System to Develop and Analyze Models of Musculoskeletal Structures, Comput. Biol. Med., vol. 25, No. 1, pp. 21-34, 1995.
Delp et al. "Computer Assisted Knee Replacement", Clinical Orthopaedics, pp. 49-56, Sep. 1998.
"Ex. AA to Smith & Nephew, Inc.'s Request for Ex Parte Reexamination of U.S. Pat. No. 8,377,129 dated Feb. 21, 2018—Ground No. 1 Claim Chart, 42 pages".
"Ex. BB to Smith & Nephew, Inc.'s Request for Ex Parte Reexamination of U.S. Pat. No. 8,377,129 dated Feb. 21, 2018—Ground No. 2 Claim Chart, 26 pages".
"Ex. CC to Smith & Nephew, Inc.'s Request for Ex Parte Reexamination of U.S. Pat. No. 8,377,129 dated Feb. 21, 2018—Ground No. 3 Claim Chart, 36 pages".
"Ex. DD to Smith & Nephew, Inc.'s Request for Ex Parte Reexamination of U.S. Pat. No. 8,377,129 dated Feb. 21, 2018—Ground No. 4 Claim Chart, 23 pages".
"Ex. EE to Smith & Nephew, Inc.'s Request for Ex Parte Reexamination of U.S. Pat. No. 8,377,129 dated Feb. 21, 2018—Ground No. 5 Claim Chart, 31 pages".
"Ex. FF to Smith & Nephew, Inc.'s Request for Ex Parte Reexamination of U.S. Pat. No. 8,377,129 dated Feb. 21, 2018—Ground No. 6 Claim Chart, 41 pages".
"Ex. GG to Smith & Nephew, Inc.'s Request for Ex Parte Reexamination of U.S. Pat. No. 8,377,129 dated Feb. 21, 2018—Ground No. 7 Claim Chart, 26 pages".
"Ex. HH to Smith & Nephew, Inc.'s Request for Ex Parte Reexamination of U.S. Pat. No. 8,377,129 dated Feb. 21, 2018—Ground No. 8 Claim Chart, 33 pages".
"Ex. II to Smith & Nephew, Inc.'s Request for Ex Parte Reexamination of U.S. Pat. No. 8,377,129 dated Feb. 21, 2018—Ground No. 9 Claim Chart, 23 pages".
"Ex. JJ to Smith & Nephew, Inc.'s Request for Ex Parte Reexamination of U.S. Pat. No. 8,377,129 dated Feb. 21, 2018—Ground No. 10 Claim Chart, 29 pages".
"Exhibit 1046 to Petition for Inter Partes Review of U.S. Pat. No. 9,216,025—English translation of EP 1074229 B1, translated Nov. 2016, 4 pages".
"Exhibit 1046 to Petition for Inter Partes Review of U.S. Pat. No. 9,295,482 (claims 1-12)—English translation of EP 1074229 A2, Jul. 2, 2001, 5 pages".
"Exhibit 1047 to Petition for Inter Partes Review of U.S. Pat. No. 9,216,025—EP 1074229 B1, Oct. 5, 2005,7 pages".
"Exhibit 1048 to Petition for Inter Partes Review of U.S. Pat. No. 9,216,025—The Miller/Galante Porous Tivanium Total Knee, Zimmer, Inc., 1984, 18 pages".
"Exhibit 1049 to Petition for Inter Partes Review of U.S. Pat. No. 9,216,025—Choice. The Miller/Galante Total Knee System, Zimmer, Inc., 1986, 17 pages".
"Exhibit 1066 to Petition for Inter Partes Review of U.S. Pat. No. 9,295,482 (claims 1-12)—Madrid et al., MR Features of Osteoarthritis of the Knee, Magnetic Resonance Imaging, 12, 1994, 7 pages".
"Exhibit 1068 to Petition for Inter Partes Review of U.S. Pat. No. 9,295,482 (claims 1-12)—Peterfy et al., "Whole-Organ Magnetic Resonance Imaging Score (WORMS) of the Knee in Osteoarthritis," OsteoArthritis and Cartilage, 12, 2004, 14 pages".
"Exhibit 1069 to Petition for Inter Partes Review of U.S. Pat. No. 9,295,482 (claims 1-12)—Excerpts from Mink et al., "Magnetic Resonance Imaging of the Knee," 1987, 21 pages".
"Exhibit AA to Smith & Nephew, Inc.'s Request for Ex Parte Reexamination of U.S. Pat. No. 9,295,482 dated Oct. 16, 2017—Ground No. 1 Claim Chart, 32 pages".
"Exhibit BB to Smith & Nephew, Inc.'s Request for Ex Parte Reexamination of U.S. Pat. No. 9,295,482 dated Oct. 16, 2017—Ground No. 2 Claim Chart, 6 pages".
"Exhibit C to Smith & Nephew, Inc.'s Request for Ex Parte Reexamination of U.S. Pat. No. 9,295,482—McCauley, et al., "Central Osteophytes in the Knee: Prevalence and Association with Cartilage Defects on MR Imaging," AJR, 2001, 6 pages".
"Exhibit CC to Smith & Nephew, Inc.'s Request for Ex Parte Reexamination of U.S. Pat. No. 9,295,482 dated Oct. 16, 2017—Ground No. 3 Claim Chart, 17 pages".
"Exhibit DD to Smith & Nephew, Inc.'s Request for Ex Parte Reexamination of U.S. Pat. No. 9,295,482 dated Oct. 16, 2017—Ground No. 4 Claim Chart, 3 pages".
"Exhibit EE to Smith & Nephew, Inc.'s Request for Ex Parte Reexamination of U.S. Pat. No. 9,295,482 dated Oct. 16, 2017—Ground No. 5 Claim Chart, 7 pages".
"Exhibit FF to Smith & Nephew, Inc.'s Request for Ex Parte Reexamination of U.S. Pat. No. 9,295,482 dated Oct. 16, 2017—Ground No. 6 Claim Chart, 2 pages".
"Exhibit GG to Smith & Nephew, Inc.'s Request for Ex Parte Reexamination of U.S. Pat. No. 9,295,482 dated Oct. 16, 2017—Ground No. 7 Claim Chart, 14 pages".
"Exhibit HH to Smith & Nephew, Inc.'s Request for Ex Parte Reexamination of U.S. Pat. No. 9,295,482 dated Oct. 16, 2017—Ground No. 8 Claim Chart, 1 page".
"Exhibit No. 1002 to Petition for Inter Partes Review of U.S. Pat. No. 7,534,263—Declaration of Jay D. Mabrey, M.D., Dec. 20, 2016, 126 pages".
"Exhibit No. 1002 to Petition for Inter Partes Review of U.S. Pat. No. 7,981,158 (claims 1-65)—Declaration of Jay D. Mabrey, M.D., Dec. 15, 2016, 136 pages".
"Exhibit No. 1002 to Petition for Inter Partes Review of U.S. Pat. No. 8,062,302—Declaration of Jay D. Mabrey, M.D., Jan. 23, 2017, 151 pages".
"Exhibit No. 1002 to Petition for Inter Partes Review of U.S. Pat. No. 8,337,129—Declaration of Jay D. Mabrey, M.D., Nov. 30, 2016, 135 pages".
"Exhibit No. 1002 to Petition for Inter Partes Review of U.S. Pat. No. 8,551,169—Declaration of Jay D. Mabrey, M.D., Nov. 27, 2016, 105 pages".
"Exhibit No. 1002 to Petition for Inter Partes Review of U.S. Pat. No. 8,657,827—Declaration of Jay D. Mabrey, M.D., Feb. 27, 2017, 150 pages".
"Exhibit No. 1002 to Petition for Inter Partes Review of U.S. Pat. No. 9,055,953—Declaration of Jay D. Mabrey, M.D., 132 pages, Sep. 16, 2016".
"Exhibit No. 1002 to Petition for Inter Partes Review of U.S. Pat. No. 9,216,025—Declaration of Jay D. Mabrey, M.D., Nov. 17, 2016, 117 pages".
"Exhibit No. 1002 to Petition for Inter Partes Review of U.S. Pat. No. 9,216,025—Declaration of Jay D. Mabrey, M.D., Oct. 20, 2016, 161 pages".

(56) References Cited

OTHER PUBLICATIONS

"Exhibit No. 1002 to Petition for Inter Partes Review of U.S. Pat. No. 9,295,482 (claims 1-12)—Declaration of Jay D. Mabrey, M.D., Nov. 29, 2016, 154 pages".
"Exhibit No. 1015 to Petition for inter Partes Review of U.S. Pat. No. 9,055,953—"A Survey of Medical Image Registration," Med. Car. Image Analysis, vol. 2, No. 1, pp. 1-37, Oct. 16, 1997".
"Exhibit No. 1017 to Petition for Inter Partes Review of U.S. Pat. No. 9,055,953—Excerpts of Patent Prosecution History pertaining to U.S. Appl. No. 12/777,809, 578 pages".
"Exhibit No. 1019 to Petition for Inter Partes Review of U.S. Pat. No. 9,055,953—Curriculum Vitae of Jay D. Mabrey, MD, 27 pages, Aug. 2, 2016".
"Exhibit No. 1021 to Petition for Inter Partes Review of U.S. Pat. No. 9,055,953—U.S. Appl. No. 60/293,488, filed May 25, 2001, 15 pages".
"Exhibit No. 1022 to Petition for Inter Partes Review of U.S. Pat. No. 9,055,953—U.S. Appl. No. 60/363,527, filed Mar. 12, 2002, 13 pages".
"Exhibit No. 1024 to Petition for inter Partes Review of U.S. Pat. No. 9,055,953—Excerpts from ConforMIS, Inc.'s Preliminary Invalidity NonInfringement Disclosures, Civil Action No. 1:16-cv-10420-IT—Document No. 60, 101 pages, Sep. 16, 2016".
"Exhibit No. 1027 to Petition for Inter Partes Review of U.S. Pat. No. 9,216,025—U.S. Appl. No. 10/160,667, filed May 28, 2002, 80 pages".
"Exhibit No. 1037 to Petition for Inter Partes Review of U.S. Pat. No. 9,216,025—Excerpts from Surgery of the Knee, Second Edition, John N. Insall, M.D., et al., 1993, 130 pages".
"Exhibit No. 1041 to Petition for Inter Partes Review of U.S. Pat. No. 9,216,025—Genesis Total Knee System, Primary Surgical Technique, 1993, 59 pages".
"Exhibit No. 1042 to Petition for Inter Partes Review of U.S. Pat. No. 9,216,025—Excerpts from Principles of Deformity Correction, Dror Paley, 2002, 21 pages".
"Exhibit No. 1045 to Petition for Inter Partes Review of U.S. Pat. No. 9,216,025—Declaration of Christine Drake re: Translation of EP 1074229 B1 dated Nov. 10, 2016, 3 pages".
Exhibit No. 1045 to Petition for Inter Partes Review of U.S. Pat. No. 9,295,482 (claims 1-12)—Declaration of Christine Drake re: Translation of EP 1074229 A2 dated Dec. 2, 2016, 3 pages.
"Exhibit No. 1058 to Petition for Inter Partes Review of U.S. Pat. No. 8,551,169—Schiffers et al. "Planning and Realization of Orthopedic Surgery with the Aid of Individual Templates" 29 Orthopäde (Orthopedist), 2000, 10 pages (In German)".
"Exhibit No. 1059 to Petition for Inter Partes Review of U.S. Pat. No. 8,551,169—Methods and Application of Three-Dimensional Imaging in Orthopedics, 109 Archives of Orthopaedic Trauma Surgery, 186, 1990, 8 pages".
"Exhibit No. 1061 to Petition for Inter Partes Review of U.S. Pat. No. 8,551,169—Manco et al., Meniscal Tears-Comparison of Arthrography, CT and MRI, 29(2), Critical Reviews in Diagnostic Imaging, 151, 1989, 34 pages".
"Exhibit No. 1064 to Petition for Inter Partes Review of U.S. Pat. No. 8,551,169—Schiffers et al. "Planning and Realization of Orthopedic Surgery with the Aid of Individual Templates" 29 Orthopäde (Orthopedist), 2000, 6 pages(English Translation)".
"Exhibit No. 1065 to Petition for Inter Partes Review of U.S. Pat. No. 8,551,169—Declaration of Michael Degn re: Translation of Schiffers et al. "Planning and Realization of Orthopedic Surgery with the Aid of Individual Templates" Nov. 29, 2016, 1 page".
"Exhibit No. 1086 to Petition for Inter Partes Review of U.S. Pat. No. 7,981,158 (claims 1-65)—Karadimitriou et al., Min-Max Compression Methods for Medical Image Databases, 26(1), SIGMOD Record 47, 1997, 8 pages".
"Exhibit No. 1087 to Petition for Inter Partes Review of U.S. Pat. No. 7,981,158 (claims 1-65)—Determining the Rotational Alignment of the Femoral Component in Total Knee Arthroplasty Using the Epicondylar Axis, 286 Clinical Orthopaedics and Related Research, 40, 1993, 15 pages".

"Exhibit No. 1095 to Petition for Inter Partes Review of U.S. Pat. No. 8,062,302—Excerpts from ConforMIS, Inc.'s Preliminary Infringement Disclosures, Civil Action No. 1:16-cv-10420-IT—Document No. 52, 56 pages, Jul. 22, 2016".
"Exhibit No. 1096 to Petition for Inter Partes Review of U.S. Pat. No. 8,657,827—Excerpts from ConforMIS,'s Opening Claim Construction Brief, Civil Action No. 1:16-cv-10420-IT—Document No. 88, 7 pages, Jan. 24, 2017".
"Exhibit No. 1102 to Petition for Inter Partes Review of U.S. Pat. No. 7,534,263—Declaration of Jay D. Mabrey, M.D., Dec. 20, 2016, 121 pages".
"Exhibit No. 1102 to Petition for Inter Partes Review of U.S. Pat. No. 7,981,158 (claims 66-81)—Declaration of Jay D. Mabrey, M.D., Dec. 15, 2016, 124 pages".
"Exhibit No. 1102 to Petition for Inter Partes Review of U.S. Pat. No. 8,062,302—Declaration of Jay D. Mabrey, M.D., Jan. 23, 2017, 159 pages".
"Exhibit No. 1102 to Petition for Inter Partes Review of U.S. Pat. No. 8,657,827—Declaration of Jay D. Mabrey, M.D., Feb. 27, 2017, 174 pages".
"Exhibit No. 1102 to Petition for Inter Partes Review of U.S. Pat. No. 9,295,482 (claims 13-20)—Declaration of Jay D. Mabrey, M.D., Nov. 29, 2016, 145 pages".
"Exhibit No. 2007 to Patent Owner Response, Case No. IPR2016-01874—Outerbridge et al., "The Etiology of Chondromalacia Patellae," The Journal of Bone and Joint Surgery, 1961, 6 pages".
"Exhibit No. 2007 to Patent Owner Response, Case No. IPR2017-00373—Sprawls, Jr., PhD., "Physical Principles of Medical Imaging," 1993, 75 pages".
"Exhibit No. 2008 to Patent Owner Response, Case No. IPR2016-01874—"Dorland's Illustrated Medical Dictionary," 27th Edition, 1988, 4 pages".
"Exhibit No. 2008 to Patent Owner Response, Case No. IPR2017-00373—Weber, et al., "How to be a "Multi-Lingual" CT Technologist: Understanding Scan Parameters from Different Manufacturer's Equipment," Mayo Clinic, 2004 RSNA Annual Meeting Poster, 1 page".
"Exhibit No. 2009 to Patent Owner Response, Case No. IPR2016-01874—Gagliardi, et al., "Detection and Staging of Chondromalacia Patellae: Relative Efficacies of Conventional MR Imaging, MR Arthography, and CT Arthrography," AJR, 1994, 8 pages".
"Exhibit No. 2012 to Patent Owner Response, Case No. IPR2016-01874—Netter, M.D., "Atlas of Human Anatomy," Section VII, Lower Limb, 1989, 62 pages".
"Exhibit No. 2023 to Patent Owner Response, Case No. IPR2017-00544—Kellgren, et al., "Radiological Assessment of Osteo-Arthrosis," Ann. Rheum. Dis., 1957, 9 pages".
Extended European Search Report—Application No. 10181149.5-1526 dated Apr. 19, 2012, 9 pages.
Extended European Search Report—Application No. 10181198.2-1526® dated Apr. 19, 2012, 9 pages.
"Final Written Decision of U.S. Pat. No. 9,216,025, Case No. IPR2017-00115, entered Apr. 19, 2018, 78 pages".
"Final Written Decision of U.S. Pat. No. 7,981,158, Case No. IPR2017-00510, Entered Jun. 11 2018, 55 pages".
"Final Written Decision of U.S. Pat. No. 7,981,158, Case No. IPR2017-00511, Entered Jun. 11 2018, 41 pages".
"Final Written Decision of U.S. Pat. No. 8,551,169, Case No. IPR2017-00373, Entered Jun. 12, 2018, 65 pages".
"Final Written Decision of U.S. Pat. No. 9,055,953, Case No. IPR2016-01874, Entered Mar. 26 2018, 61 pages".
Hafez et al. "Computer Assisted Total Knee Replacement: Could a Two-Piece Custom Template Replace the Complex Conventional Instrumentations?", 4th Annual Meeting of CAOS Int'l Proc., Chicago, Jun. 16-19, 2004, pp. 63-64.
Hafez et al. "Computer Assisted Total Knee Replacement: Could a Two-Piece Custom Template Replace the Complex Conventional Instrumentations?" Session 6: Novel Instruments; Computer Aided Surgery, Session 6, vol. 9, No. 3, pp. 93-94 (Jun. 2004).
Hafez et al. "Computer-Assisted Total Hip Arthroplasty: The Present and the Future", Future Rheumatol., vol. 1, pp. 121-131, 2006.

(56) References Cited

OTHER PUBLICATIONS

Hafez et al. "Computer-assisted Total Knee Arthroplasty Using Patient-specific Templating," Clinical Orthopaedics and Related Research, No. 444, pp. 184-192 (Mar. 2006).
"Hofmann et al. "Effect of the Tibial Cut on Subsidence Following Total Knee Arthroplasty," Clinical Orthopaedics and Related Research, No. 269, pp. 63-69, Aug. 1991".
"Inter Partes Review Certificate, U.S. Pat. No. 7,981,158, Case No. IPR2017-00510, dated Feb. 22, 2019, 2 pages".
"Inter Partes Review Certificate, U.S. Pat. No. 8,551,169, Case No. IPR2017-00373, dated Feb. 26, 2019, 2 pages".
International Search Report International Application No. PCT/US2007/061681, dated Sep. 7, 2007, together with the Written Opinion of the International Searching Authority, 12 pages.
International Search Report—International Application No. PCT/US2013/025216 dated May 30, 2013, together with the Written Opinion of the International Searching Authority, 12 pages.
International Search Report—International Application No. PCT/US2014/030001 dated Aug. 27, 2014, together with the Written Opinion of the International Searching Authority, 10 pages.
International Search Report—International Application No. PCT/US2015/012203 dated May 4, 2015, together with the Written Opinion of the International Searching Authority, 12 pages.
Kidder J. et al.3D Model Acquisition Design Planning and Manufacturing of Orthopaedic Devices: A Framework Proceedings of the SPIE Advanced Sensor and Control-System Interface Boston MA vol. 2911 pp. 9-22 (Nov. 21, 1996).
"Krackow, Kenneth A., "The Technique of Total Knee Arthroplasty", The C. V. Mosby Company, excerpt from book—pp. 49-237, 1990".
Kshirsagar et al.Measurement of Localized Cartilage Volume and Thickness of Human Knee Joints by Computer Analysis of Three-Dimensional Magnetic Resonance Images Invest Radiol. May;33(5): 289-299 1998 T. 111 V. III.
Lombardi, Jr. et al. "Patient-Specific Approach in Total Knee Arthroplasty", Orthopedics, vol. 31, Issue 9, Sep. 2008, 8 pages.
"McCauley et al. "Central Osteophytes in the Knee: Prevalence and Association with Cartilage Defects on MR Imaging", American Journal of Roentgenology, No. 176, pp. 359-364, Feb. 2001".
"Menkes, MD et al. "Are osteophytes good or bad?," Osteoarthritis and Cartilage, OsteoArthritis Research Society International, vol. 12, pp. S53-S54, 2004".
"Smith & Nephew, Inc.'s Reply to Patent Owner's Response of U.S. Pat. No. 9,055,953, Case No. IPR2016-01874, Filed Sep. 13, 2017, 33 pages".
"Smith & Nephew, Inc.'s Request for Ex Parte Reexamination of U.S. Pat. No. 8,377,129, filed Feb. 21, 2018, 151 pages".
"Smith & Nephew, Inc.'s Request for Ex Parte Reexamination of U.S. Pat. No. 9,295,482, filed Oct. 16, 2017, 107 pages".
"Moseley, MD et al. "A Controlled Trial of Arthroscopic Surgery for Osteoarthritis of the Knee," The New England Journal of Medicine, vol. 347, No. 2, pp. 81-88, Jul. 11, 2002".
Office Action dated Feb. 13, 2014, pertaining to U.S. Appl. No. 13/306,501, 25 pages.
"Office Action in Ex Parte Reexamination of U.S. Pat. No. 9,295,482, dated Apr. 18, 2018, 18 pages".
"Order Granting Ex Parte Reexamination of U.S. Pat. No. 9,295,482, Control No. 90/014,036, Nov. 22, 2017, 15 pages".
"Patent Owner's Notice of Appeal, Case No. IPR2016-01874, U.S. Pat. No. 9,055,953, filed May 25, 2018, 68 pages".
"Patent Owner's Notice of Appeal, Case No. IPR2017-00115, U.S. Pat. No. 9,216,025, filed Jun. 7, 2018, 85 pages".
"Patent Owner's Preliminary Response, Case No. IPR2017-00307, U.S. Pat. No. 9,216,025, filed Apr. 28, 2017, 59 pages".
"Patent Owner's Preliminary Response, Case No. IPR2017-00373, U.S. Pat. No. 8,551,169, filed Mar. 15, 2017, 52 pages".
"Patent Owner's Preliminary Response, Case No. IPR2017-00488, U.S. Pat. No. 9,295,482, filed Apr. 11, 2017, 39 pages".
"Patent Owner's Preliminary Response, Case No. IPR2017-00510, U.S. Pat. No. 7,981,158, filed Apr. 20, 2017, 32 pages".
"Patent Owner's Preliminary Response, Case No. IPR2017-00511, U.S. Pat. No. 7,981,158, filed Apr. 20, 2017, 30 pages".
"Patent Owner's Preliminary Response, Case No. IPR2017-00544, U.S. Pat. No. 7,534,263, filed Apr. 17, 2017, 45 pages".
"Patent Owner's Preliminary Response, Case No. IPR2017-00545, U.S. Pat. No. 7,534,263, filed Apr. 17, 2017, 57 pages".
"Patent Owner's Preliminary Response, Case No. IPR2017-00778, U.S. Pat. No. 8,062,302, filed May 9, 2017, 20 pages".
"Patent Owner's Preliminary Response, Case No. IPR2017-00779, U.S. Pat. No. 8,062,302, filed May 9, 2017, 40 pages".
"Patent Owner's Preliminary Response, Case No. IPR2017-00780, U.S. Pat. No. 8,062,302, filed May 9, 2017, 31 pages".
"Patent Owner's Preliminary Response, Case No. IPR2017-00983, U.S. Pat. No. 8,657,827, filed Jun. 14, 2017, 44 pages".
"Patent Owner's Preliminary Response, Case No. IPR2017-00984, U.S. Pat. No. 8,657,827, filed Jun. 14, 2017, 42 pages".
"Patent Owner Response to Petition for Inter Partes Review of U.S. Pat. No. 7,534,263, Case No. IPR2017-00544, filed Oct. 24, 2017, 83 pages".
"Patent Owner Response to Petition for Inter Partes Review of U.S. Pat. No. 7,981,158, Case No. IPR2017-00510, filed Oct. 23, 2017, 52 pages".
"Patent Owner Response to Petition for Inter Partes Review of U.S. Pat. No. 7,981,158, Case No. IPR2017-00511, filed Oct. 23, 2017, 49 pages".
"Patent Owner Response to Petition for Inter Partes Review of U.S. Pat. No. 8,062,302, Case Nos. IPR2017-00778 & IPR2017-00779 and IPR2017-00780, filed Oct. 24, 2017, 84 pages".
"Patent Owner Response to Petition for Inter Partes Review of U.S. Pat. No. 8,551,169, Case No. IPR2017-00373, filed Oct. 23, 2017, 69 pages".
"Patent Owner Response to Petition for Inter Partes Review of U.S. Pat. No. 9,055,953, Case No. IPR2016-01874, filed Jun. 23, 2017, 82 pages".
"Patent Owner Response to Petition for Inter Partes Review of U.S. Pat. No. 9,216,025, Case No. IPR2017-00115, filed Jul. 19, 2017, 86 pages".
"Patent Owners Preliminary Response, Case No. IPR2017-00372, U.S. Pat. No. 8,377,129, filed Mar. 15, 2017, 40 pages".
"Patent Owners Preliminary Response, Case No. IPR2017-00487, U.S. Pat. No. 9,295,482, filed Apr. 11, 2017, 42 pages".
"Perry et al. "Spontaneous recovery of the joint space in degenerative hip disease," Annals of the Rheumatic Diseases, vol. 31, pp. 440-448, May 2, 1972".
"Petition for Inter Partes Review of U.S. Pat. No. 7,534,263, Case No. IPR2017-00544, filed Dec. 27, 2016, 99 pages".
"Petition for Inter Partes Review of U.S. Pat. No. 7,534,263, Case No. IPR2017-00545, filed Dec. 27, 2016, 99 pages".
"Petition for Inter Partes Review of U.S. Pat. No. 7,981,158 (claims 1-65), Case No. IPR2017-00510, filed Dec. 20, 2016, 93 pages".
"Petition for Inter Partes Review of U.S. Pat. No. 7,981,158 (claims 66-81), Case No. IPR2017-00511, filed Dec. 20, 2016, 96 pages".
"Petition for Inter Partes Review of U.S. Pat. No. 8,062,302, Case No. IPR2017-00778, filed Jan. 26, 2017, 97 pages".
"Petition for Inter Partes Review of U.S. Pat. No. 8,062,302, Case No. IPR2017-00779, filed Jan. 26, 2017, 92 pages".
"Petition for Inter Partes Review of U.S. Pat. No. 8,062,302, Case No. IPR2017-00780, filed Jan. 26, 2017, 106 pages".
"Petition for Inter Partes Review of U.S. Pat. No. 8,337,129, Case No. IPR2017-00372, filed Nov. 30, 2016, 99 pages".
"Petition for Inter Partes Review of U.S. Pat. No. 8,551,169, Case No. IPR2017-00373, filed Nov. 30, 2016, 80 pages".
"Petition for Inter Partes Review of U.S. Pat. No. 8,657,827, Case No. IPR2017-00983, filed Feb. 28, 2017, 101 pages".
"Petition for Inter Partes Review of U.S. Pat. No. 8,657,827 (claims 50-64), Case No. IPR2017-00984, filed Feb. 28, 2017, 106 pages".
"Petition for Inter Partes Review of U.S. Pat. No. 9,216,025, Case No. IPR2017-00115, filed Oct. 20, 2016, 108 pages".
"Petition for Inter Partes Review of U.S. Pat. No. 9,216,025, Case No. IPR2017-00307, filed Nov. 21, 2016, 102 pages".
"Petition for Inter Partes Review of U.S. Pat. No. 9,295,482 (claims 1-12), Case No. IPR2017-00487, filed Dec. 14, 2016, 106 pages".

(56) References Cited

OTHER PUBLICATIONS

"Petition for Inter Partes Review of U.S. Pat. No. 9,295,482 (claims 13-20), Case No. IPR2017-00488, filed Dec. 14, 2016, 115 pages".
"Petitioner Smith & Nephew's Reply to Patent Owner Conformis's Response of U.S. Pat. No. 7,981,158, Case No. IPR2017-00510, filed Jan. 25, 2018, 34 pages".
"Petitioner Smith & Nephew's Reply to Patent Owner Conformis's Response of U.S. Pat. No. 7,981,158, Case No. IPR2017-00511, filed Jan. 25, 2018, 35 pages".
"Petitioner Smith & Nephew's Reply to Patent Owner Conformis's Response of U.S. Pat. No. 8,551,169, Case No. IPR2017-00373, filed Jan. 25, 2018, 35 pages".
"Petitioner Smith & Nephew Reply to Patent Owner Conformis Response to Petition for Inter Partes Review of U.S. Pat. No. 9,216,025, Case No. IPR2017-00115, filed Oct. 23, 2017, 34 pages".
"Petitioner Smith & Nephew's Reply to Patent Owner Conformis's Response to Petition of U.S. Pat. No. 7,534,263, Case No. IPR2017-00544, filed Mar. 2, 2018, 33 pages".
"Petitioner Smith & Nephew's Reply to Patent Owner Conformis's Response to Petition of U.S. Pat. No. 8,062,302, Case Nos. IPR2017-778, IPR2017-779 and IPR2017-780, filed Mar. 2, 2018, 35 pages".
Portheine et al. "Computer-Assisted Total Knee Endoprosthetics with Planning-Specific Treatment Templates", Biomed. Tech., vol. 46, Supp. vol. 1, Jan. 2001—English translation.
Portheine et al. "Computer-Assisted Total Knee Endoprosthetics with Planning-Specific Treatment Templates", Biomed. Tech., vol. 46, Supp. vol. 1, Jan. 2001—In German.
Portheine et al CT-Based Planning and Individual Template Navigation in TKA Navigation and Robotics in Total Joint and Spine Surgery Springer 48:336-342 (2004).
Portheine et al. Development of a clinical demonstrator for computer assisted orthopedic surgery with CT-image based individual templates Computer Assisted Radiology and Surgery (1997).
Portheine et al. "Potentials of CT-based Planning and Template-based Procedure in Hip and Knee Surgery", Orth. Prac., vol. 36, pp. 786-791, 2000—English Translation.
Portheine et al. "Potentials of CT-based Planning and Template-based Procedure in Hip and Knee Surgery", Orth. Prac., vol. 36, pp. 786-791, 2000—In German.
Portheine thesis : "Model-Based Operation Planning in Orthopedic Surgery", Thesis, RWTH Aachen University, Apr. 22, 2004, 90 pages—In German.
Portheine thesis "Model-Based Operation Planning in Orthopedic Surgery", Thesis, RWTH Aachen University, Apr. 22, 2004, 170 pages—English Translation.
"Pottenger et al. "The Effect of Marginal Osteophytes on Reduction of Varus-Valgus Instability in Osteoarthritic Knees," Arthritis and Rheumatism, vol. 33, No. 6, pp. 853-858, Jun. 1990".
Proskauer Rose LLP, Counsel for ConforMIS, Inc., United States District Court of Massachusetts, Civil Action No. 16-10420—Document No. 1—Plaintiff's Complaint for Patent Infringement—ConforMIS, Inc., without exhibits, 14 pages, 2016.
Radermacher "Computer Assisted Matching of Planning and Execution in Orthopedic Surgery", Slide Presentation, San Diego, Nov. 29, 1993, 22 pages.
Radermacher "Computer-Based Decision Support in the Selection and Evaluation of Contact Surfaces for Manual Referencing", Lecture presented at Helmholtz Meeting '98 and OSS '98, 6 pages(1998)—® In German.
Radermacher "Computer-Based Decision Support in the Selection and Evaluation of Contact Surfaces for Manual Referencing", Lecture presented at Helmholtz Meeting '98 and OSS '98, 8 pages(1998)—English Translation.
Radermacher et al. Image Guided Orthopedic Surgery Using Individual Templates Experimental Results and Aspects of the Development of a Demonstrator for Pelvis Surgery in Troccaz J. Grimson E., Mosges R (eds). Computer Vision, Virtual Reality and Robotics in Medicine and Medical Robotics and Computer Assisted Surgery, Lecture Notes in Computer Science. Berlin, Springer-Verlag 606-616, 1997.
Radermacher et al. "Computer Assisted Matching of Planning and Execution in Orthopedic Surgery", IEEE, EMBS, San Diego, 1993, pp. 946-947.
Radermacher et al. "Computer Assisted Orthopedic Surgery by Means of Individual Templates Aspects and Analysis of Potential Applications •" Proceedings of the First International Symposium on Medical Robotics and Computer Assisted Surgery, vol. 1: Sessions I-III, MRCAS '94, Pittsburgh, PA, pp. 42-48 (Sep. 22-24, 1994).
Radermacher et al. "Computer Based Decision Support for the Planning of Contact Faces for Manual Registration with Individual Templates", Helmholtz-Institute for Biomed. Eng., 7 pages, 1997-1998.
Radermacher et al. "Computer Integrated Advanced Orthopedics (CIAO)", 2nd European Conference on Eng. And Med., presented Apr. 26, 1993, 12 pages.
Radermacher et al. "Computer Integrated Surgery—Connecting Planning and Execution of Surgical Intervention in Orthopedics", Surgical Therapy Technology, Helmholtz-Institut Aachen Research Report, 1991-1992, pp. 187, 196-202.
Radermacher et al. "Computer-assisted operative interventions in orthopedics—are there prospects for endoprosthetics as well?", Prac. Ortho., vol. 27, pp. 1-17, 1997—English Translation.
Radermacher et al. "Computer-assisted operative interventions in orthopedics—are there prospects for endoprosthetics as well?", Prac. Ortho., vol. 27, pp. 149-164, 1997—In German.
Radermacher et al. "Computer-Assisted Planning and Operation in Orthopedics", Orth. Prac. 36th year, pp. 731-737, Dec. 2000—English Translation.
Radermacher et al. "Computer-Assisted Planning and Operation in Orthopedics", Orth. Prac. 36th year, pp. 731-737, Dec. 2000—In German.
Radermacher, et al. CT Image Based Planning and Execution of Interventions in Orthopedic Surgery Using Individual Templates Experimental Results and a spects of Clinical Applications. In Nolte LP, Ganz, R. (eds). CAOS Computer Assisted Orthopaedic Surgery. Bern, Hans Huber (in Press) 1998.
Radermacher et al. Technique for Better Execution of CT Scan Planned Orthopedic Surgery on Bone Structures. In Lemke HW Inamura K. Jaffe CC Vannier MW (eds). Computer Assisted Radiology Berlin Springer 933-938 1995.
Radermacher et al. "Surgical Therapy Technology", Helmholtz-Institut Aachen Research Report, 1993-1994, pp. 189-219.
Radermacher "Image Guided Orthopedic Surgery with Individual Templates", Helmhotz-Institute for Biomed. Eng., 2 pages, 1997.
Radermacher K. et al. Computer Integrated Orthopedic Surgery Connection of Planning and Execution in Surgical Inventions. In Taylor R. Lavallee S. Burdea G. Mosges R. (eds). Computer Integrated Surgery. Cambridge MIT press 451-463 1996.
Radermacher Klaus Computer Assisted Orthopaedic Surgery With Image Based Individual Templates Clinical Orthopaedics Sep. 1998 vol. 354 pp. 28-38.
Radermacher Klaus English Translation: Helmholtz Institute of Biomedical Technology Computer-Assisted Planning and Execution of Orthopedic Surgery Using Individual Surgical Templates May 18, 1999.
Radermacher Klaus German Version: Helmholtz Institute of Biomedical Technology Computer-Assisted Planning and Execution of Orthopedic Surgery Using Individual Surgical Templates May 18, 1999.
Radermacher "Template Based Navigation—An Efficient Technique for Hip and Knee Surgery", CAOS First Asian Meet, India, Mar. 27-28, 2004, pp. 44-50.
Rau et al. "Small and Neat", Medical Tech. Int'l, pp. 65, 67 and 69, 1993-1994.
Schiffers et al. "Planning and execution of orthopedic surgery using individualized templates," Der Orthopäde, Springer-Verlag, vol. 29, No. 7, pp. 636-640, (Jul. 2000) (In German).

(56) References Cited

OTHER PUBLICATIONS

Schiffers et al. "Planning and execution of orthopedic surgery using individualized templates," Der Orthopäde, Springer-Verlag, vol. 29, No. 7, pp. 636-640, (Jul. 2000) (English Translation with Certification).

Staudte et al. "Computer-Assisted Operation Planning and Technique in Orthopedics", North Rhine-Westphalia Acad. For Sciences, Lecture N.444, ISSN 0944-8799, 2000, 17 pages—In German.

Staudte et al. "Computer-Assisted Operation Planning and Technique in Orthopedics", North Rhine-Westphalia Acad. For Sciences, Lecture N.444, ISSN 0944-8799, 2000, 34 pages—English Translation.

Thoma et al. "Custom-made knee endoprosthetics using subtraction data of three-dimensional CT scans—A new approach," Der Orthopäde, Springer-Verlag, vol. 29, No. 7, pp. 641-644, (Jul. 2000) (In German).

Thoma et al. "Custom-made knee endoprosthetics using subtraction data of three-dimensional CT scans—A new approach," Der Orthopäde, Springer-Verlag, vol. 29, No. 7, pp. 641-644, (Jul. 2000)(English Translation with Certification).

Thoma et al. "Use of a New Subtraction Procedure Based on Three-Dimensional CT Scans for the Individual Treatment of Bone Defects in the Hip and Knee," Journal DGPW, No. 17, pp. 27-28 (May 1999) (In German).

Thoma et al. "Use of a New Subtraction Procedure Based on Three-Dimensional CT Scans for the Individual Treatment of Bone Defects in the Hip and Knee," Journal DGPW, No. 17, pp. 27-28 (May 1999)(English Translation with Certification).

"United States Court of Appeals for the Federal Circuit—Judgment affirming PTAB's decision in IPR2016-01874 and IPR2017-00115 filed Sep. 10, 2019, 2 pages".

"United States District Court for the District of Massachusetts, Civil Action No. 1:16-cv-10420-IT—Order Granting Stipulation of Dismissal, dated Sep. 24, 2018, 1 page".

"United States District Court of Delaware, Civil Action No. 1:19-cv-01528-RGA—Document No. 1—Plaintiff's Complaint for Patent Infringement—*Conformis, Inc.* v. *Zimmer Biomet Holdings, Inc. et al.*. filed Aug. 15, 2019, 207 pages".

"United States District Court of Delaware, Civil Action No. 1:19-cv-01528-RGA—Document No. 14—Defendant's Motion to Dismiss the Complaint for Failure to State a Claim Pursuant to Fed. R. Civ. P. 12(b)(6)—*Conformis, Inc.* v. *Zimmer Biomet Holdings, Inc. et al.* filed Jan. 13, 2020, 3 pages".

"United States District Court of Delaware, Civil Action No. 1:19-cv-01528-RGA—Document No. 15—Defendant's Opening Brief in Support of Motion to Dismiss the Complaint for Failure to State a Claim Pursuant to Fed. R. Civ. P. 12(b)(6)—*Conformis, Inc.* v. *Zimmer Biomet Holdings, Inc. et al.* filed Jan. 13, 2020, 18 pages".

"United States District Court of Delaware, Civil Action No. 1:19-cv-01528-RGA—Document No. 19—Plaintiff's Amended Complaint for Patent Infringement—*Conformis, Inc.* v. *Zimmer Biomet Holdings, Inc. et al.* filed Feb. 3, 2020, 37 pages".

"United States District Court of Delaware, Civil Action No. 1:19-cv-01528-RGA—Document No. 20—Defendant's Answer and Counterclaims to Plaintiff's Amended Complaint for Patent Infringement—*Conformis, Inc.* v. *Zimmer Biomet Holdings, Inc. et al.* filed Feb. 18, 2020, 26 pages".

"United States District Court of Delaware, Civil Action No. 1:19-cv-01528-RGA—Document No. 57—Stipulation of Partial Dismissal—*Conformis, Inc.* v. *Zimmer Biomet Holdings, Inc. et al.*, filed May 29, 2020, 2 pages".

"United States District Court of Delaware, Civil Action No. 1:19-cv-01618-RGA—Document No. 1—Plaintiff's Complaint for Patent Infringement—*Conformis, Inc.* v. *Medacta USA, Inc.* filed Aug. 29, 2019, 26 pages".

"United States District Court of Delaware, Civil Action No. 1:19-cv-01618-RGA—Document No. 13—Defendant's Answer to the Complaint—*Conformis, Inc.* v. *Medacta USA, Inc.* filed Dec. 2, 2019, 31 pages".

"United States District Court of Delaware, Civil Action No. 1:19-cv-01618-RGA—Document No. 15—Plaintiff's Amended Complaint for Patent Infringement—*Conformis, Inc.* v. *Medacta USA, Inc.* filed Dec. 23, 2019, 30 pages".

"United States District Court of Delaware, Civil Action No. 1:19-cv-01618-RGA—Document No. 16—Defendant's Answer to the Amended Complaint—*Conformis, Inc.* v. *Medacta USA, Inc.* filed Jan. 6, 2020, 36 pages".

"United States District Court of Delaware, Civil Action No. 1:19-cv-01618-RGA—Document No. 85—Plaintiff's Second Amended Complaint for Patent Infringement—*Conformis, Inc.* v. *Medacta USA, Inc.* et al., filed Oct. 14, 2020, 34 pages".

"United States District Court of Delaware, Civil Action No. 1:19-cv-01618-RGA—Document No. 89—Medacta's Answer to the Second Amended Complaint for Patent Infringement—*Conformis, Inc.* v. *Medacta USA, Inc. et al.*, filed Oct. 28, 2020, 42 pages".

"United States District Court of Delaware, Civil Action No. 1:19-cv-01618-RGA—Medacta USA, Inc.'s Invalidity Contentions with Respect to U.S. Pat. No. 8,377,129; U.S. Pat. No. 8,460,304; U.S. Pat. No. 9,186,161; and U.S. Pat. No. 9,295,482 dated Jul. 22, 2020, 15 pages".

"United States District Court of Delaware, Civil Action No. 1:99-mc-09999—Document No. 1—Plaintiff's Complaint for Patent Infringement—*Conformis, Inc.* v. *Wright Medical Technology, Inc. et al.* filed Apr. 24, 2020, 28 pages".

"United States District Court of Massachusetts, Civil Action No. 1:16-cv-10420-IT—Document No. 104—Smith & Nephew's Responsive Claim Construction Brief Regarding Terms in ConforMIS Patents, 127 pages, Feb. 24, 2017".

"United States District Court of Massachusetts, Civil Action No. 1:16-cv-10420-IT—Document No. 106—ConforMIS's Responsive Claim Construction Brief, 33 pages, Feb. 24, 2017".

"United States District Court of Massachusetts, Civil Action No. 1:16-cv-10420-IT—Document No. 59—Smith & Nephew, Inc.'s Preliminary Invalidity Disclosures, without exhibits, 36 pages, Sep. 16, 2016".

"United States District Court of Massachusetts, Civil Action No. 1:16-cv-10420-IT—Document No. 86—Smith & Nephew's Opening Claim Construction Brief, without exhibits, 41 pages, Jan. 24, 2017".

"United States District Court of Massachusetts, Civil Action No. 1:16-cv-10420-IT—Document No. 88—ConforMIS's Opening Claim Construction Brief, 80 pages, Jan. 24, 2017".

United States District Court of Massachusetts, Civil Action No. 13-12312—Document No. 1—Plaintiff's Complaint for Patent Infringement—ConforMIS, Inc., 406 pages, 2013.

United States District Court of Massachusetts, Civil Action No. 13-12312—Document No. 18—Defendant's Answer, Affirmative Defenses and Counterclaims to Plaintiff's Complaint—Wright Medical Technology, Inc. et al., 17 pages, 2013.

United States District Court of Massachusetts, Civil Action No. 13-12312—Document No. 31—Plaintiff's First Amended Complaint for Patent Infringement—ConforMIS, Inc., 543 pages, 2014.

United States District Court of Massachusetts, Civil Action No. 13-12312—Document No. 34—Plaintiff and Counterclaim Defendant's Answer to Counterclaims—ConforMIS, Inc., 5 pages, 2014.

United States District Court of Massachusetts, Civil Action No. 13-12312—Document No. 35—Defendant's Answer, Affirmative Defenses and Counterclaims to Plaintiff's First Amended Complaint for Patent Infringement—Wright Medical Technology, Inc. et al., 24 pages, 2014.

United States District Court of Massachusetts, Civil Action No. 13-12312—Document No. 44—Plaintiff and Counterclaim Defendant's Answer to Amended Counterclaims—ConforMIS, Inc., 6 pages, 2014.

United States District Court of Massachusetts, Civil Action No. 13-12312—Document No. 52—Defendant MicroPort Orthopedics, Inc.'s Answer, Affirmative Defenses, and Counterclaims to Plaintiff's First Amended Complaint for Patent Infringement—MicroPort Orthopedics, Inc., 22 pages, 2014.

United States District Court of Massachusetts, Civil Action No. 13-12312—Document No. 53—Plaintiff and Counterclaim Defendant's Answer to MicroPort Orthopedics Inc.'s Counterclaims—ConforMIS, Inc., 5 pages, 2014.

(56) References Cited

OTHER PUBLICATIONS

United States District Court of Massachusetts, Civil Action No. 13-12312-FDS—Document No. 55—Defendants' Preliminary Invalidity and Non-Infringement Disclosures—Wright Medical Technology, Inc. et al. 22 pages, 2014.

"United States Patent and Trademark Office, Before the Patent Trial and Appeal Board—Case No. IPR2016-01874, Petition for Inter Partes Review of U.S. Pat. No. 9,055,953, 102 pages, Sep. 21, 2016".

"Supplemental Patent Owner's Response, Case No. IPR2017-00544, U.S. Pat. No. 7,534,263, filed Jun. 29, 2018, 40 pages".

"Supplemental Patent Owner's Response, Case Nos. IPR2017-00778, IPR2017-00779, IPR2017-00780, U.S. Pat. No. 8,062,302 filed Jun. 29, 2018, 46 pages".

"Whiteside, MD et al., "The Effect of Posterior Tibial Slope on Knee Stability After Ortholoc Total Knee Arthroplasty", The Journal of Arthroplasty, Oct. 1988 Supplement, pp. S51-S57".

"Yau et al. "Residual Posterior Femoral Condyle Osteophyte Affects the Flexion Range after Total Knee Replacement", International Orthopaedics (SCIOT) vol. 29, pp. 375-379, May 12, 2005".

\* cited by examiner

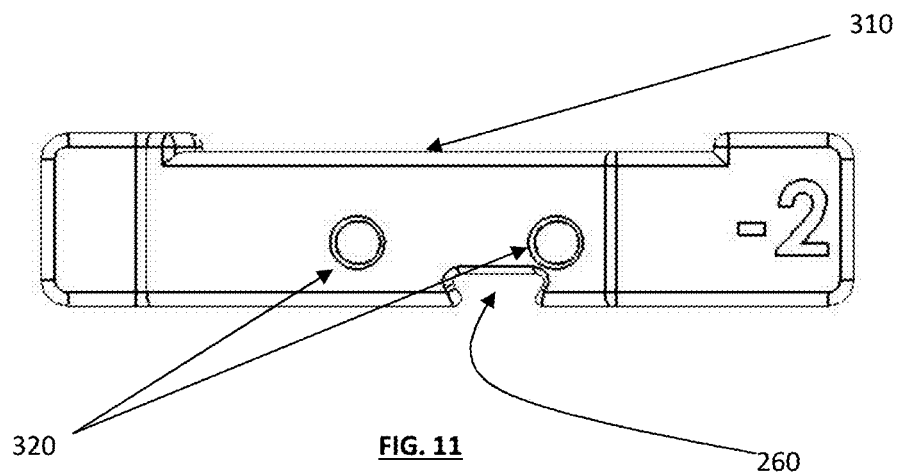
FIG. 11
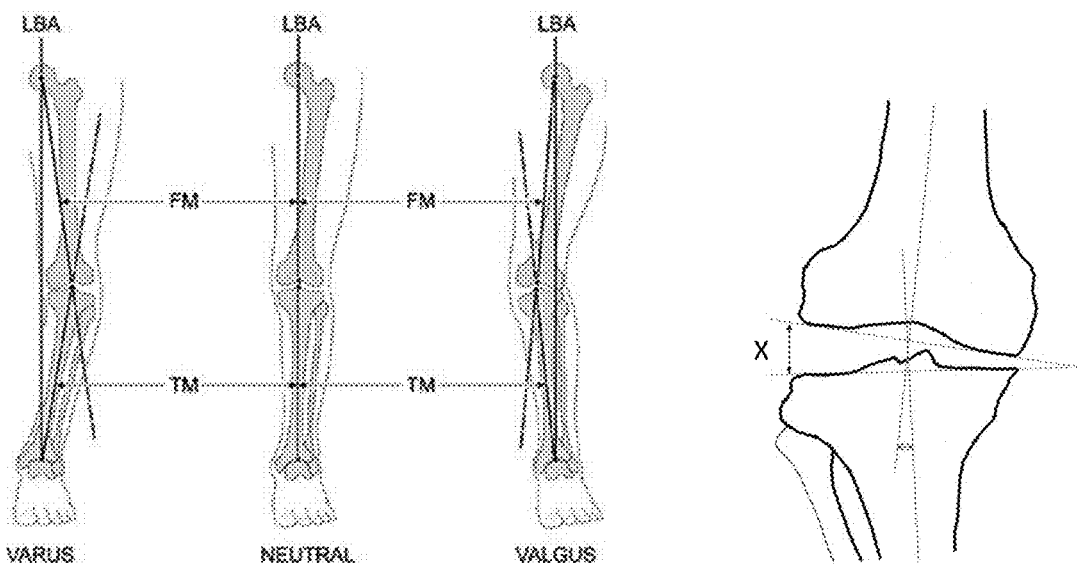
FIG. 12A
FIG. 12B
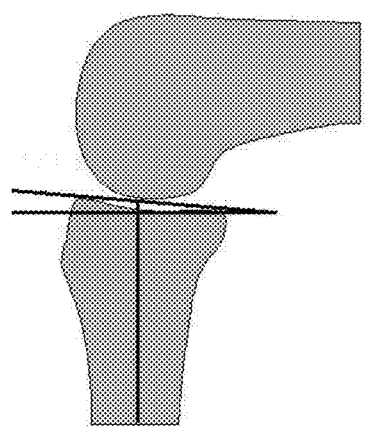
FIG. 12C

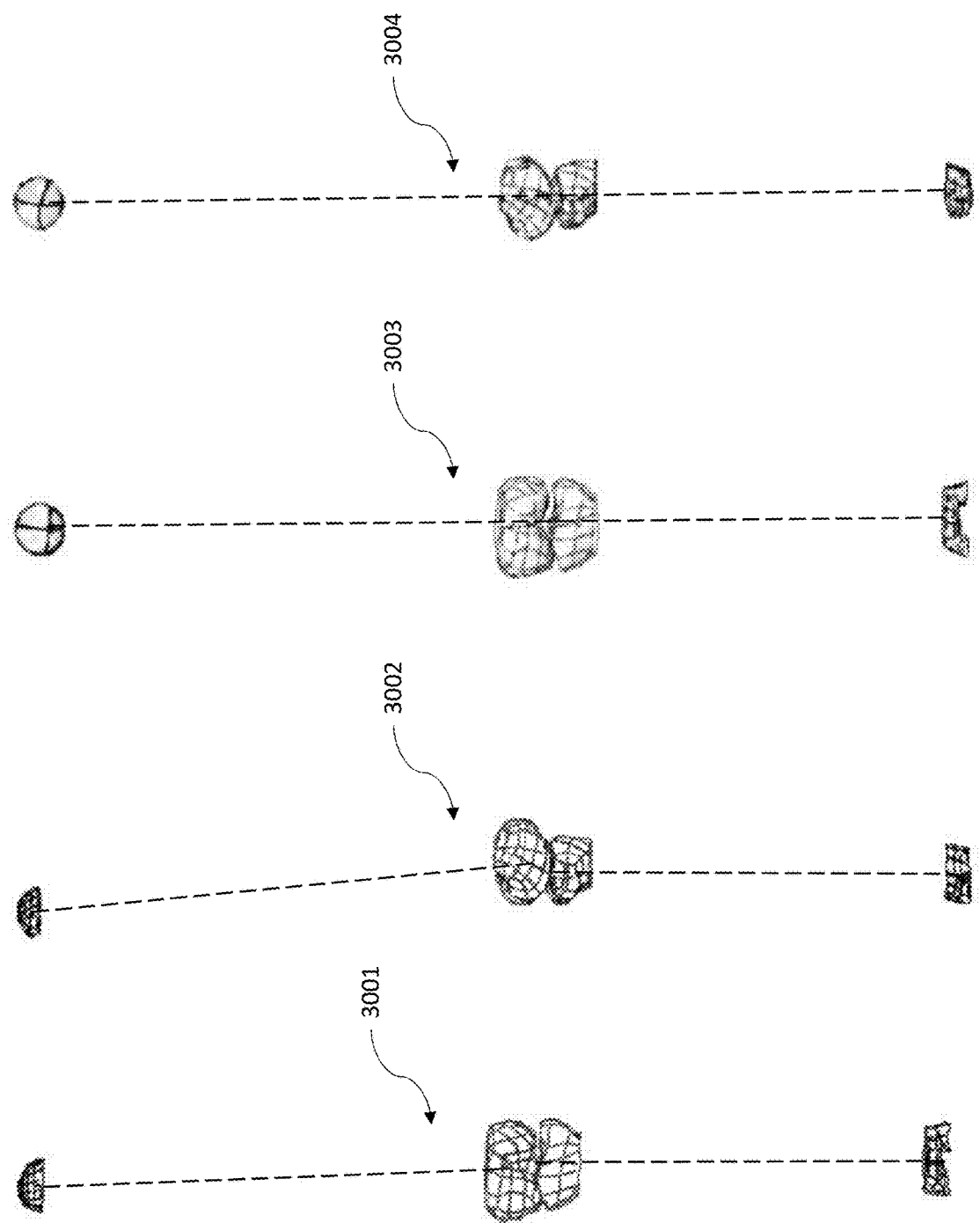

TIBIAL GUIDES, TOOLS AND TECHNIQUES FOR RESECTING THE TIBIAL PLATEAU

RELATED APPLICATIONS

This application is a continuation of U.S. application Ser. No. 15/330,828, entitled "Tibial Guides, Tools, and Techniques for Resecting the Tibial Plateau" and filed Nov. 7, 2016, which in turn is a continuation of U.S. application Ser. No. 13/865,958, entitled "Tibial Guides, Tools, and Techniques for Resecting the Tibial Plateau" and filed Apr. 18, 2013, which in turn claims the benefit of U.S. Provisional Application Ser. No. 61/635,270, entitled "Tibial Guides, Tools, and Techniques for Resecting the Tibial Plateau" and filed Apr. 18, 2012, the disclosure of each which is incorporated herein by reference in its entirety.

TECHNICAL FIELD

This disclosure relates to improved and/or patient-adapted (e.g., patient-specific and/or patient-engineered) surgical guides, tools and techniques to assist with the resection of the tibial plateau or similar bones. More specifically, the present disclosure provides a set of alignment and cutting guides and methods for use that are easier and more reliable for use by experienced and inexperienced knee surgeons.

BACKGROUND

When a patient's knee is severely damaged, such as by osteoarthritis, rheumatoid arthritis, or post-traumatic arthritis, it may be desirous to repair and/or replace portions or the entirety of the knee with a total or partial knee replacement implant. Knee replacement surgery is a well-tolerated and highly successful procedure that can help relieve pain and restore function in injured and/or severely diseased knee joints.

In a typical knee surgery, the surgeon will begin by making an incision through the various skin, fascia, and muscle layers to expose the knee joint and laterally dislocate the patella. The anterior cruciate ligament may be excised and/or the surgeon may choose to leave the posterior cruciate ligament intact—such soft tissue removal often depends on the surgeon's preference and condition(s) of the ACL/PCL. Various surgical techniques are used to remove the arthritic joint surfaces, and the tibia and femur are prepared and/or resected to accept the component artificial implants.

Preparing the surface of the tibia often requires that the surgeon resect the articular surface of the bone to receive an implant over the resected surface. The resection can include specific depths of cut(s), posterior slope(s), varus/valgus angle(s), and/or axial alignment(s) that can be unique to every patient. The specific dimensions and/or measurements desirably ensure proper positioning of the artificial joint component assembly, and accurate guiding and cutting of the tibial plateau is important to achieve the most accurate and best fit of the artificial implant components.

Traditionally, a surgeon has two options to help them prepare the tibia. The surgeon may select the traditional "freehand" method, or he/she may choose a set of surgical instruments that will assist with positioning, resection and alignment. The "freehand" method usually involves standard surgical tools available in the operating room (OR) during surgery, such as osteotomy drills and calipers for measuring. The procedure, preparation, alignment and/or resection may be more or less accurate, depending on the level of the skill and/or ability of the surgeon. Where surgical guide tools are chosen, the surgeon may employ a standard sized saw guide block or other resection guides, which desirably assist with the critical cuts required in the tibial plateau. A saw guide block or resection guide can first be attached to the patient in various ways, and then an alignment device can be used to provide a desired alignment. Once the resection guide is aligned, it can be temporarily fixed in place on the anterior side of the tibia, and the alignment device removed to allow the cutting or resection operation. While the use of such standard sized guide blocks or resection guides can improve the surgical procedure, they may not provide sufficient fine adjustments for cutting depth and/or slope, may be bulky, and may not be easy to use. The misuse or non-use of such devices can result in improper depth of cut, improper posterior slope, malalignment of varus/valgus angle(s), and poor axial alignment that may contribute to poor artificial implant positioning, instability of the joint, and poor surgical outcomes.

As a result, it has been recognized that it would be desirable to provide a more effective system of guides, tools, instruments and methods to facilitate a high degree of success in the preparation of the tibial plateau to receive an artificial joint.

SUMMARY

Some disclosed embodiments include a tibial guide housing for use in treatment of a tibia. The tibial guide housing can include a first reference arm with a patient-specific contact surface configured to conform to a first portion of the superior surface of the tibia. The tibial guide housing can also include a second reference arm having a patient-specific contact surface configured to conform to a second portion of the superior surface of the tibia. Additionally, the tibial guide housing can include at least one pin hole configured to accommodate insertion of a pin through the tibial guide housing and into the tibia. The tibial guide housing can also include a patient-specific contact surface configured to conform to a portion of an anterior surface of the tibia.

Some embodiments can include a system for preparing a tibial plateau. The system can include a tibial guide housing and one or more tibial cutting guide boxes, each of the one or more tibial cutting guide boxes. The tibial cutting guide boxes can include a patient-specific contact surface configured to conform to a portion of the anterior surface of the tibia. The tibial cutting guide boxes can also include a guide aperture configured to accommodate a surgical cutting tool and guide the cutting tool along a cutting plane having a predetermined cut depth and angle. Additionally, the tibial cutting guide boxes can include at least one pin hole configured to accommodate a pin passing into the tibia.

These and other objects, advantages, and features of the disclosure will be apparent from the following description, considered along with the accompanying drawings.

BRIEF DESCRIPTION OF THE SEVERAL VIEWS OF THE DRAWING

FIG. 11 depicts a front view of a "minus two cut depth" tibial guide box;

FIGS. 12A-12C depicts various views of a knee joint at neutral, varus and valgus angles, depicting possible posterior slopes of the knee;

FIG. 29 illustrates a virtual model of a patient's limb that is misaligned in the sagittal plane, and a virtually corrected limb.

DETAILED DESCRIPTION

Figure 1:
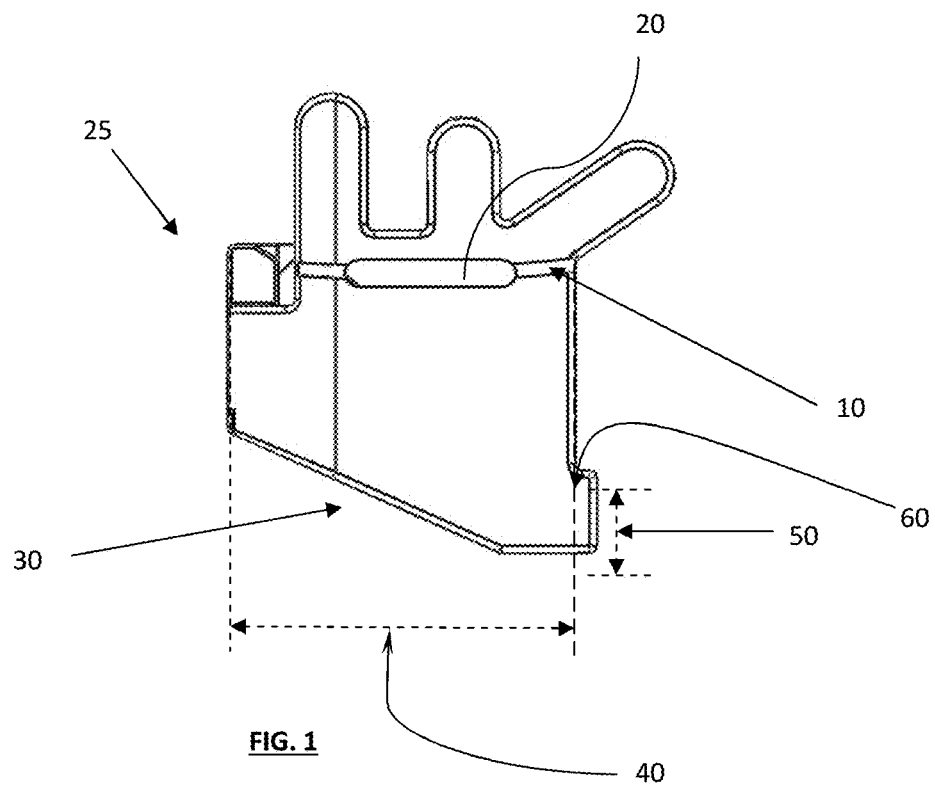
FIG. 1 depicts a top plan view of one embodiment of a tibial guide housing and/or body.

The present disclosure provides an improved patient-specific or patient-engineered tibial resection guide alignment apparatus (hereinafter "resection guide") and associated methods that desirably overcome and/or address various disadvantages of existing systems, as well as provide for controlled depth and/or slope cuts on the tibia. Various embodiments of the present disclosure may be used to facilitate total knee surgery, bicompartmental knee surgery or unicompartmental knee surgery. In addition, the various embodiments can be used for cruciate retaining surgeries or non-cruciate retaining surgeries.

Various embodiments of the present disclosure may be patient-specific or patient engineered for each surgical patient, with each tibial resection guide alignment apparatus tailored to an individual patient's joint morphology. In at least one preferred embodiment, the system may be designed as an assembly that comprises a patient specific tibial resection housing and/or body and several patient specific sized cutting blocks that can be inserted into the housing/body and used for resecting the tibial plateau.

In various embodiments, each piece of the tibial resection guide assembly can be uniquely tailored to an individual patient's anatomy, which may require images taken from the subject. The manufacturer can then design the patient-specific resection guide using the joint image from a patient or subject, wherein the image may include both normal cartilage and diseased cartilage; reconstructing dimensions of the diseased cartilage surface to correspond to normal cartilage (using, for example, a computer system) and/or bones; and designing the tibial resection guide to exactly or substantially match the dimensions of the diseased cartilage surface, the normal cartilage surface, a healthy cartilage surface, a subchondral bone surface, and/or various combinations thereof (including height, width, length, and/or reference points of the resection guide). In various alternative embodiments, the guide may substantially match an area slightly greater than the diseased cartilage surface or bone surface (or any other known size that may be applied to any patient).

The image can be, for example, an intraoperative image including a surface and/or feature detection method using any techniques known in the art, e.g., mechanical, optical, ultrasound, and known devices such as MRI, CT, ultrasound, and other image techniques known in the art. In certain embodiments, reconstruction is performed by obtaining a surface that follows the contour of the normal cartilage or the natural anatomy of the bone. The surface can be parametric and include control points that extend the contour of the normal cartilage to the diseased cartilage and/or a B-spline surface to determine the shape of at least one contact surface of the tibial resection guide to fill the areas of diseased cartilage. The images can be 2D or 3D or combination thereof to specifically design the tibial resection guide assembly.

In various embodiments, tibial resection guide assemblies constructed in accordance with various teachings described herein may be designed as extramedullary or intramedullary. Exemplary extramedullary guides or tools can be connected outside the patient's tibia, and may be designed to include an attachment for alignment rods or any other alignment mechanisms. Exemplary intramedullary alignment guides or tools can include an intramedullary rod that positioned into the central canal of the tibia with the alignment mechanism suspended from the rod.

Various embodiments can include a patient specific housing and/or body designed to include various reference points that correspond to a patient specific articular contact surface and/or subchondral bone surface (or other surface, as desired). These reference points may be perpendicular extensions or "fingers" that extend from the body to provide tibial surface anchoring. These reference points may include at least one extension, finger or arm that incorporates at least one patient specific contact surface on the articular or other surface of the tibia. The reference points may be designed to have varied lengths onto the surface of the tibia, or may be shortened to the minimum anchoring required. The reference points may be designed centrally located or can be offset to varying degrees to provide an optimal natural conforming location on the articular or other surface of the tibia to allow for stable resection.

The tibial resection guide assembly can further include one or more guide boxes that may be removably attached to the surface. The boxes may be designed to include various patient specific contact surfaces to easily mate with the anterior surface of the bone. The boxes may have at least one guide aperture for guiding a surgical cutting instrument for controlled resection of the tibia plateau. The guide boxes may also be designed to make cuts that are parallel, non-parallel, perpendicular, or non-perpendicular to other cuts.

The tibial guide boxes can be designed as removable or permanent. If the tibial guide boxes are removable, they may have a sliding mechanism that allows for easy insertion into the tibial guide resection housing and/or body. They may include other connection arrangements, including rail systems, quick connects, or other similar mechanisms for insertion into and/or connection to the guide resection housing and/or body.

Various aspects of the disclosed embodiments may be used and/or applied to a variety of other joints, such as the shoulder, hip, and wrist.

Tibial Guide Assembly Apparatus

Described herein are various embodiments of surgical tools and methods for accurately preparing the medial and lateral tibial plateau such that the plane of each cut across the bone ends will be appropriate to receive the portions of a knee prosthesis selected to reflect the spacing distance and size of the respective bone ends, so that one or more artificial knee joint components will properly and optimally replace the mechanical functioning of a normal knee.

In various embodiments, the tibial plateau preparation assembly can include: a tibial guide housing, one or more tibial cutting guide boxes with a cutting platform with a tibial depth resection guide, and optional attachment of an alignment rod. In practice, a surgeon, after opening and/or accessing the damaged knee area, may use the tibial guide assembly to prepare medial and lateral ends of a patient's tibia to receive appropriate knee components, such as a tibial tray and insert.

FIG. 1 depicts a top view of a tibial guide housing and/or body 25. The tibial housing is equipped with a variety of features that will assist the surgeon in his preparation of the tibial plateau; it is designed with a viewing window 20, an alignment indicator 10, an angled low profile body 30 and 40 and ergonomic features 50 and 60. First, the tibial guide housing contains a viewing window 20 to assist the surgeon in placement on the anterior surface of the tibia. This window will allow the surgeon to view the peripheral edge of the anterior surface of the tibia. The window, as depicted in FIG. 1, is designed substantially similar to the width of the tibial guide housing because it maximizes viewing capacity, but may be designed to have a smaller width or a larger height to accommodate the surgeon's need. The dimensions of this window may be designed as standard sizes or shapes or may be patient-specific to accommodate the tibial anatomy. The window may be a variety of shapes such as "Z," or curved shaped, or "L" shaped.

A second feature is the alignment indicator 10. This indicator provides the surgeon with visual assistance that the housing is firmly planted on the anterior surface of the tibia. The present tibial guide housing has the alignment indicator 10 designed as a small channel. However, the manufacturer may choose to design this indicator on the surface of the housing with additional visual indicators such as an arrow. The alignment indicator may be any size, shape or dimension. The alignment indicator may also be designed as patient specific to match or substantially match the perimeter of the tibia.

The tibial guide housing may be designed to have a low profile for surgery. A design that is low profile has many advantages because there is often minimal space available above and/or adjacent to the tibia during cruciate ligament retaining procedures. The angled front 30 of the tibial guide housing achieves this purpose. Also, the width 40 of the housing is also smaller than other available cutting guides. The width of the housing 40 minimizes the profile of the cutting guide and may be designed as patient specific.

The tibial guide housing may be designed to have ergonomic features, such as the extension tab 50 and radiused edges 60. The extension tab 50 allows the surgeon to grasp and handle the tibial guide housing by its edge. The edges within the extension tab are radiused 60 to provide for easy finger transition and no sharp edges. The width of this extension may be designed with varying heights or shapes. The manufacturer may design this with a "U" shape or other variety of shapes to accommodate holding of the housing.

Figure 2:
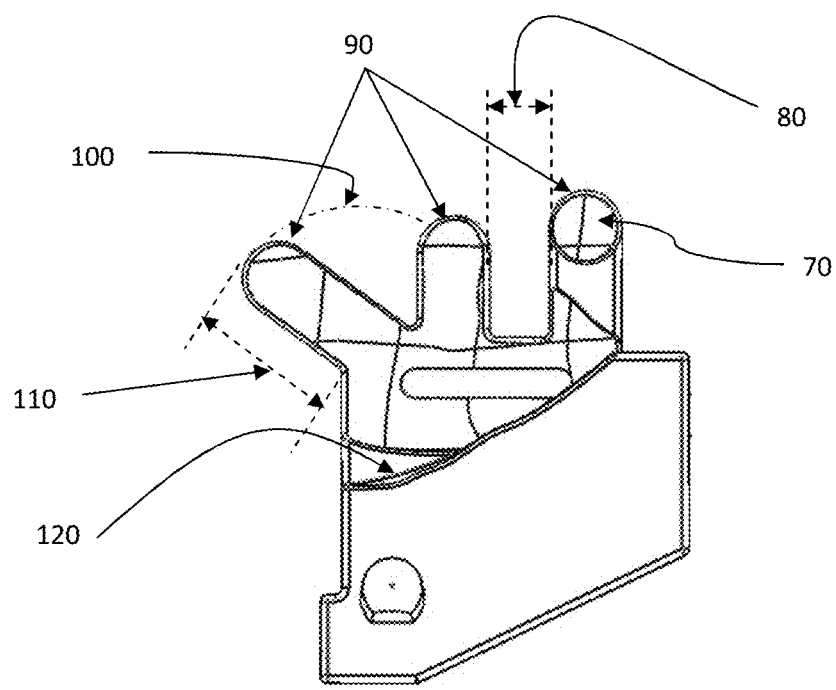
FIG. 2 depicts a bottom plan view of the tibial guide housing of FIG. 1.

FIG. 2 depicts a bottom view of the tibial guide housing, showing the reference arms 90, and the patient-specific contact surfaces 70 and 120. The tibial guide housing may be designed with specific reference extensions/arms 90 to help the surgeon find the natural, conforming position for more accurate resection. If the surgeon is resecting the medial side of the tibial plateau, the surgeon will place the reference arms 90 on the articular surface of the tibia and move it around until the reference arms finds their own natural, conforming position(s). The reference arms may be designed with at least one reference arm, but in various preferred embodiments can include three reference arms. The reference arms may respectively be titled as the "medial reference arm," which may align with the center of the medial tibial plateau, the "center reference arm," which can align between the tibial spines, and the "left reference arm," which can align with the center of the tibia. Each reference arm can be made patient specific or be made with standard available sizes retrieved from a database. The reference arms spacing 80 may vary with every patient, or a set spacing may be designed or incorporated between each reference arm. In addition, the medial reference arm and the center reference arm may also have patient-specific angles 100 designed into the housing, or angles 100 may be set standard angles derived from a database. The length 110 of each reference arm may also vary between each patient (i.e., be a patient-specific length). In various embodiments, the tibial guide housing surfaces 120 and 70 that contact the anterior portions of the tibia will be patient specific to provide a secure and conforming fit.

Figure 3:
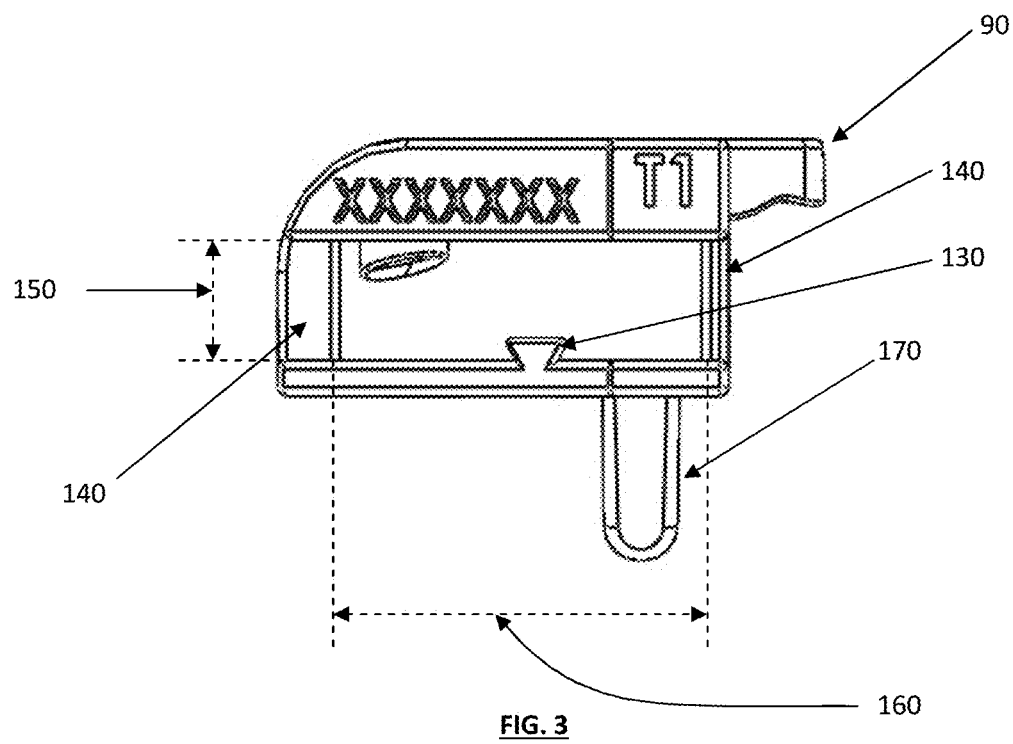
FIG. 3 depicts a front view of the tibial guide housing of FIG. 1.

FIG. 3 depicts a front view of the tibial guide housing. The front view highlights specific features such as the dovetail rail 130, the alignment rod attachment 170, the low profile width 160 and height 150 for tibial guide box insertion, and the tibial guide box positive stops 140. The dovetail rail 130 is designed within the tibial guide housing to allow and/or facilitate easy insertion and securement of the tibial guide boxes (see FIG. 8A-8C). This also allows locking of the tray into the housing and prevents any unnecessary motion or movement during cutting. The tibial guide boxes may be secured into the tibial guide housing using any mechanism that is known in the art. If desired, the tibial guide boxes may be secured by inserting the boxes into the housing and securing by set screws, by press fit, by snap tabs, or other equivalent mechanisms. Alternatively, the bottom may be designed with a recessed tray that seats the tibial guide box.

The tibial guide housing height 150 and width 160 may be designed specifically to fit one or more of the tibial guide cutting boxes. The dimensions may be minimized to provide a low profile for the assembly, or they may have different shapes to facilitate insertion of the guide boxes. The dimensions may also be patient-specific. The height 150 and/or width 160 may vary depending on the morphology or other features of the damaged or diseased tibia and articular surfaces. The tibial guide housing may also provide positive stop walls 140 to prevent the tibial guide boxes from sliding forward or other directions as well as to potentially prevent the surgeon from over-exerting pressure during insertion. The surgeon can insert the guide box into the guide housing until it reaches a detent or stop to provide accurate alignment. The tibial guide housing may also include an alignment leg 170 to allow attachment of the tibial alignment rod to the body.

Figure 4:
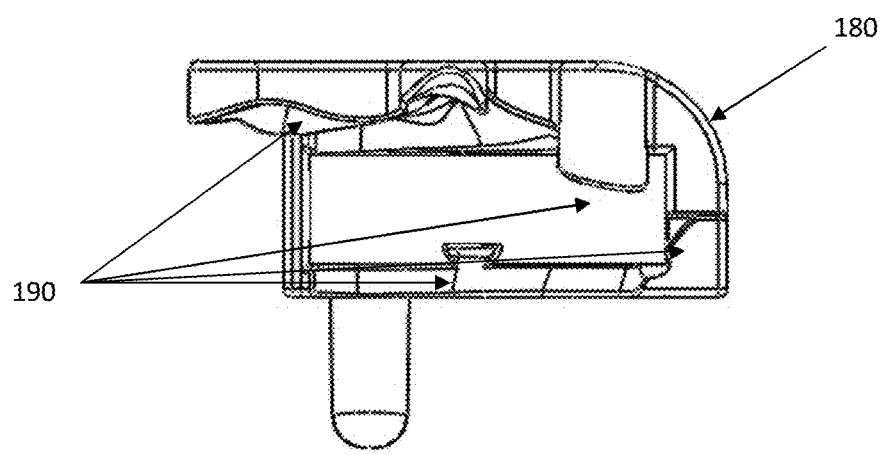
FIG. 4 depicts a back view of the tibial guide housing of FIG. 1.

FIG. 4 depicts a back view of the tibial guide housing and highlights the patient contact surfaces 190 and the curved exterior wall 180. The contact surfaces 190 may be patient specific. The image data evaluated to manufacture the housing can be used to design the surface that contacts or mates with the articular surface of the tibial plateau, thus having or approximating a patient specific shape(s). Such features can allow stability and more secure attachment when resecting or cutting is taking place. The exterior wall can be radiused 180, as desired, to eliminate, reduce or minimize soft tissue irritation.

Figure 5:
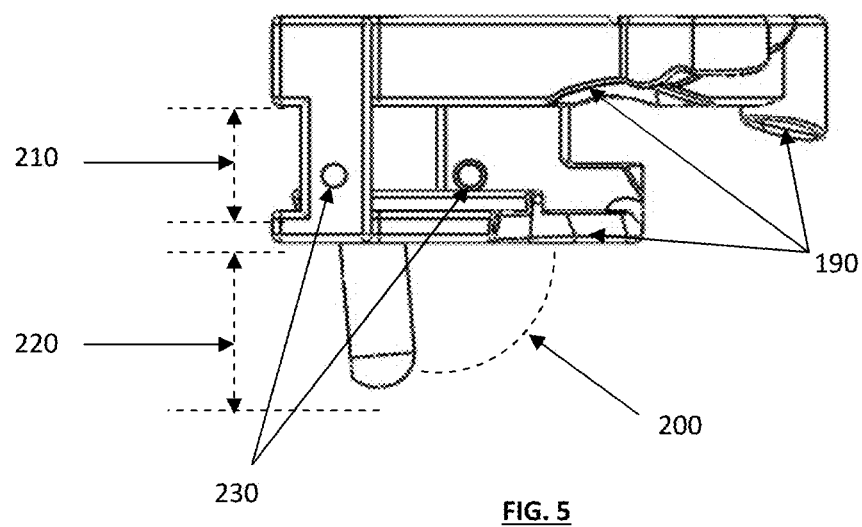
FIG. 5 depicts a right-side view of the tibial guide housing of FIG. 1.

FIG. 5 depicts a right-side view of the tibial guide housing and/or body. In this view, various detent receiver holes 230 are shown. These detent receiver holes 230 can receive a tibial guide insert box, and in various embodiments the successful insertion can be accompanied by an audible sound or other indication to the surgeon when the box is secured in place. The detent receiver holes 230 can be designed as a receiver for tabs, levers, etc., or they may have different shapes. The alignment leg angle 200 and the alignment leg 220 are also shown in this view. The angle and the length of the alignment leg may be designed as patient specific for increased accuracy in the alignment of the housing to the center axis of the tibia. The alignment leg angle 200 and the height 220 may also be designed as standard dimensions that can be determined from evaluations from a database of various patients. The alignment leg may also be designed to include various connection types, including press fit insertion. For easy removal, the alignment leg may include a quick release/connection mechanism for the surgeon's use that can prevent excessive upward force on the tibial guide housing. This side view also highlights an example of the patient specific nature of the contact surfaces 190 of the tibial guide housing.

Figure 6:
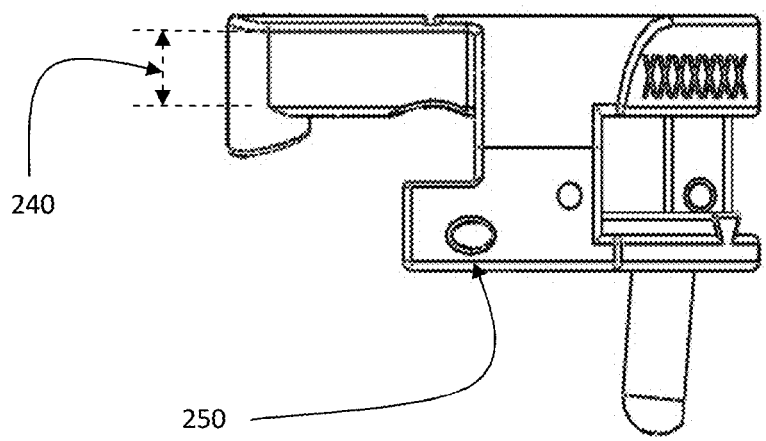
FIG. 6 depicts a left-side view of the tibial guide housing of FIG. 1.
Figure 7:
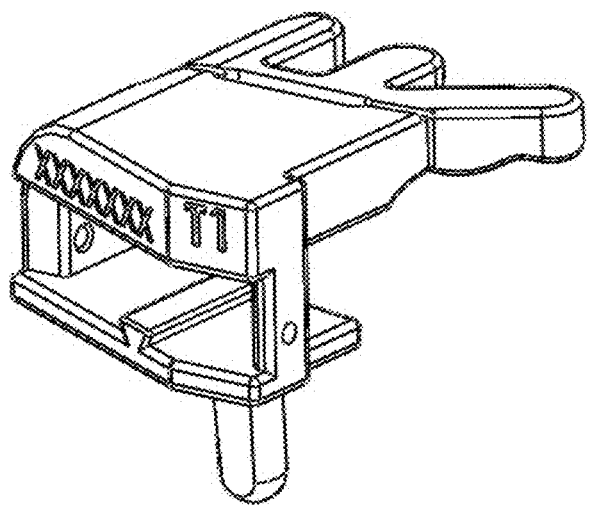
FIG. 7 depicts an isometric perspective view of the tibial guide housing of FIG. 1.

FIG. 6 depicts a left-side view of the tibial guide housing and/or body. This view highlights the relative thickness/height 240 of a reference arm, as well as an exemplary pin hole 250. The reference arm thickness/height 240 may be designed as patient specific. Each reference arm may have different thicknesses/heights to accommodate the diseased patient's surface. The thickness/height of each arm may also be designed to have standard dimensions as derived from a database of similar patients. The tibial guide housing may have one or more pin holes 250 to help secure the housing to the tibia. The pin holes may be designed large enough to accommodate a drill and to insert pins for visual guidance or location on the tibia.

Figure 8A:
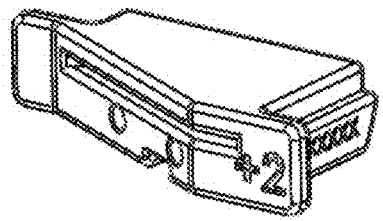
FIGS. 8A-8C depict isometric perspective views of different embodiments of tibial guide boxes having various cut depths constructed in accordance with the teaching of the present invention.
Figure 8B:
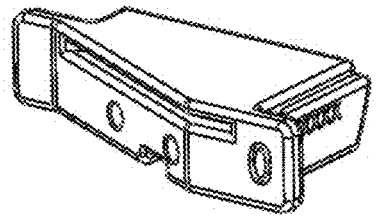
Figure 8C:
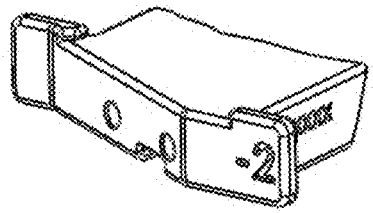

FIGS. 8A-8C depict isometric perspective views of various embodiments of different tibial guide boxes that can be used with various features disclosed herein, with various available cut depths included in one preferred embodiment. FIG. 8A shows the "+2" tibial guide box that can be employed by the surgeon to make a primary cut to the tibia. This box, along with other system features, desirably facilitates the surgeon's ability to adjust the resection or cut of the tibial plateau after a primary cut has been completed. In the embodiment shown in FIG. 8B, the primary cut can be defined as the "0" tibial guide box. In various procedures, the "0" guide box will be inserted and utilized by the surgeon to make the primary cut and may be, in various embodiments, a patient-specific selected or derived depth. FIG. 8C shows a "−2" guide box which can also allow the surgeon to adjust the cut after the primary cut has been made. Many other cut depths can be created to allow the surgeon to make additional controlled depth cuts on the tibial plateau.

Figure 9:
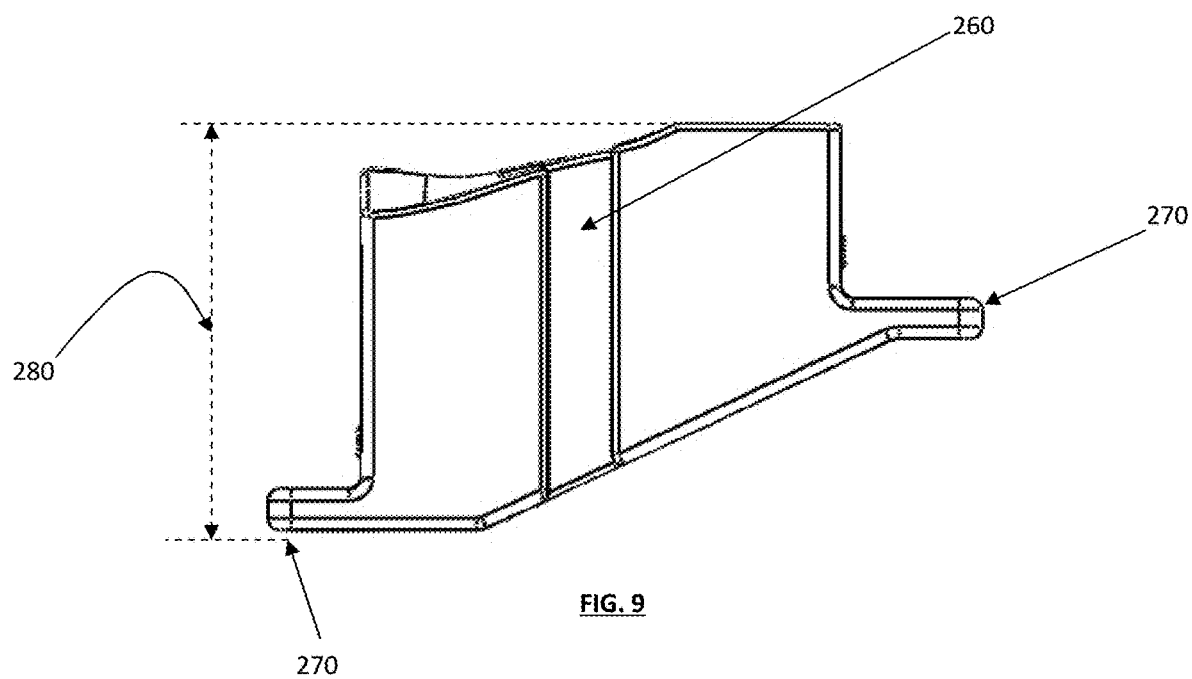
FIG. 9 depicts a bottom plan view of a tibial guide box.
Figure 10:
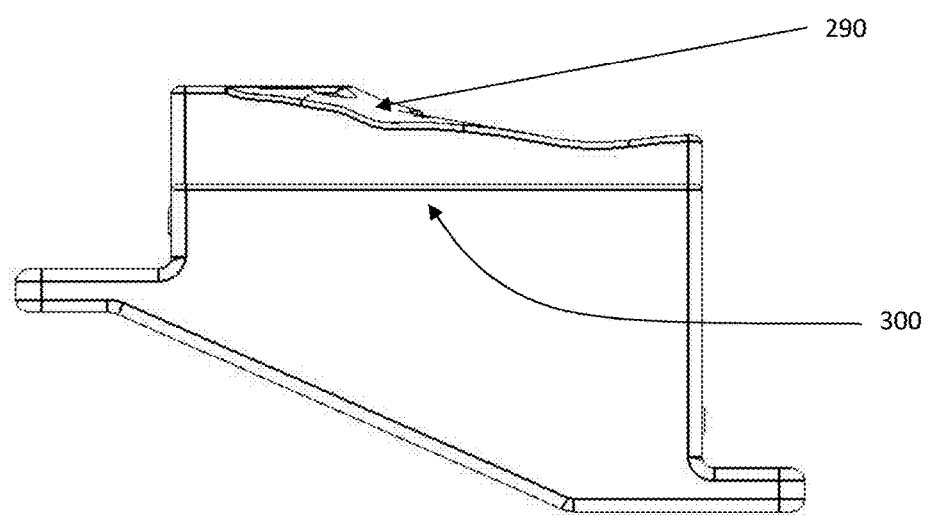
FIG. 10 depicts a top plan view of a tibial guide box.

FIGS. 9 and 10 depict the bottom and top plan views, respectively, of a tibial guide box. In these embodiments, the bottom view of the guide box shows a dovetail rail 260, and the positive stop tabs 270. The dovetail rail 260 may have varying widths or lengths for quick and guided insertion of the tibial guide boxes. The positive stop tabs 270 are designed to extend to contact the positive stop walls 140. FIG. 10 shows that the cut guide cover 300 need not necessarily extend the full depth of the tibial guide box. However, the cut guide cover may be designed to reach the entire length/depth of the tibial guide box. In addition, the cut guide cover may be manufactured out of variety of materials that would withstand an oscillating or reciprocating saw. It can be manufactured out of biocompatible metals and/or plastics.

FIG. 11 depicts a front view of a minus two cut depth guide box. This specific guide cut box need not necessarily have a cut guide cover 300 because it can use the roof of the tibial guide housing as a portion of the cut guide cover. In contrast, FIGS. 8A and 8B depict guide cut covers 300 that are designed in portions of the boxes. FIG. 11 further depicts two pin holes 320 that may be incorporated into the design of each tibial guide cut box. The tibial guide box may have pin holes 320 to help secure the box to the tibia. The pin holes may be designed large enough to accommodate a drill and to insert pins for visual guidance or location on the tibia. Also, additional pin holes may be designed into the guide box or guide housing. As previously noted, the "−2" guide box still can guide 310 the reciprocating saw or the oscillating saw by using the roof the tibial guide housing as a guide boundary. This guided slot 310 may be manufactured to specific dimensions to accommodate standard oscillating or reciprocating bone saws. In another embodiment, the guided slot 310 may also incorporate various angles, shaped and/or configurations, including different features to accommodate different varus/valgus (see FIG. 13) and/or anterior/posterior angles (see FIG. 12C) designed within the box.

Figure 13A:
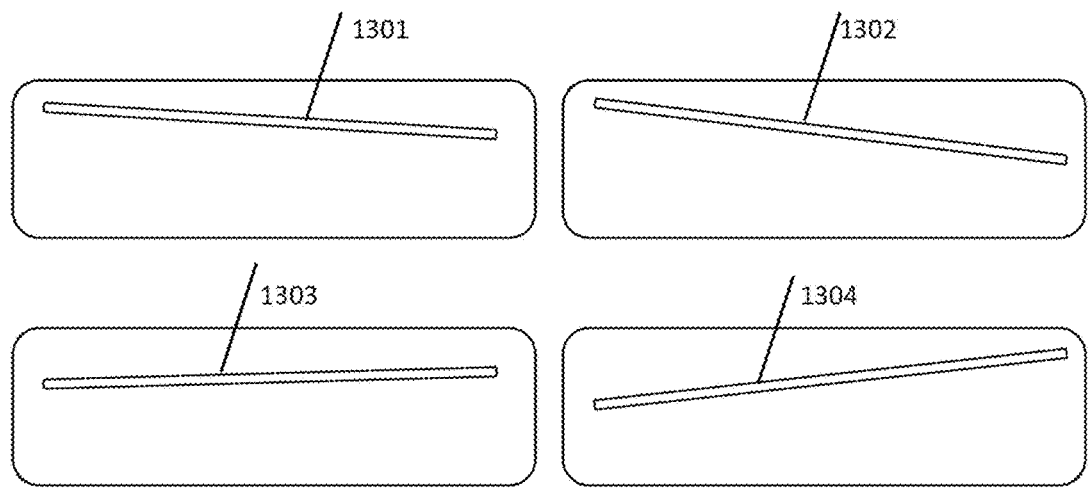
FIGS. 13A and 13B generally depict various examples varus and valgus guide cut slots that can be designed as standard and/or adjustable features, for adjusting varus/valgus angles.
Figure 13B:
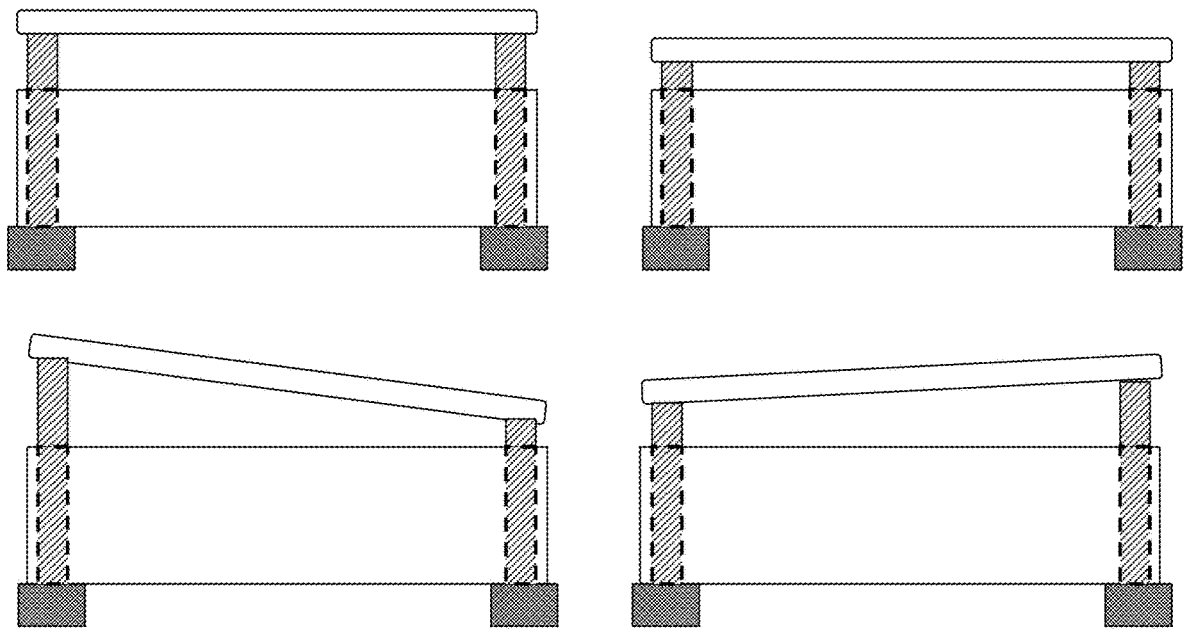

FIGS. 12A and 12B depict a human knee with exemplary varus, neutral and valgus orientations, and various exemplary angles that a cut guided slot 30 or other tool may incorporate to accommodate and/or correct such orientations. In a varus knee, this line passes medial to the knee and a moment arm is created, which increases force across the medial compartment of the knee. In a valgus knee, the load-bearing axis (LBA) passes lateral to the knee, and the resulting moment arm increases force across the lateral compartment of the knee. In various embodiments, specifically designed tibial guide boxes that incorporate patient specific varus/valgus angles could be employed to reduce and/or correct such deformities, desirably reducing abnormal forces in the artificial knee joint, and returning the LBA to a normal functioning knee at its neutral position. FIG. 13A depicts various cut guide slot angulations that, when used in conjunction with a tibial guide box as described herein, can generally be employed to alter the resulting varus or valgus angles of one or more tibial cut planes. FIG. 13B depicts one alternative embodiment of a guide tool that incorporates an adjustment mechanism 322 that can be employed and adjusted to alter the cut angle. The adjustment mechanism could include a screw thread or other mechanism that allows a wide variation in the cut plane angle, which could include larger wedges to accommodate more severe varus/valgus angles. In various embodiment, the guide tool with the adjustable mechanism could be sized and configured to fit into the standard guided slots 1301-1304 as shown in FIG. 13A.

Figure 24:
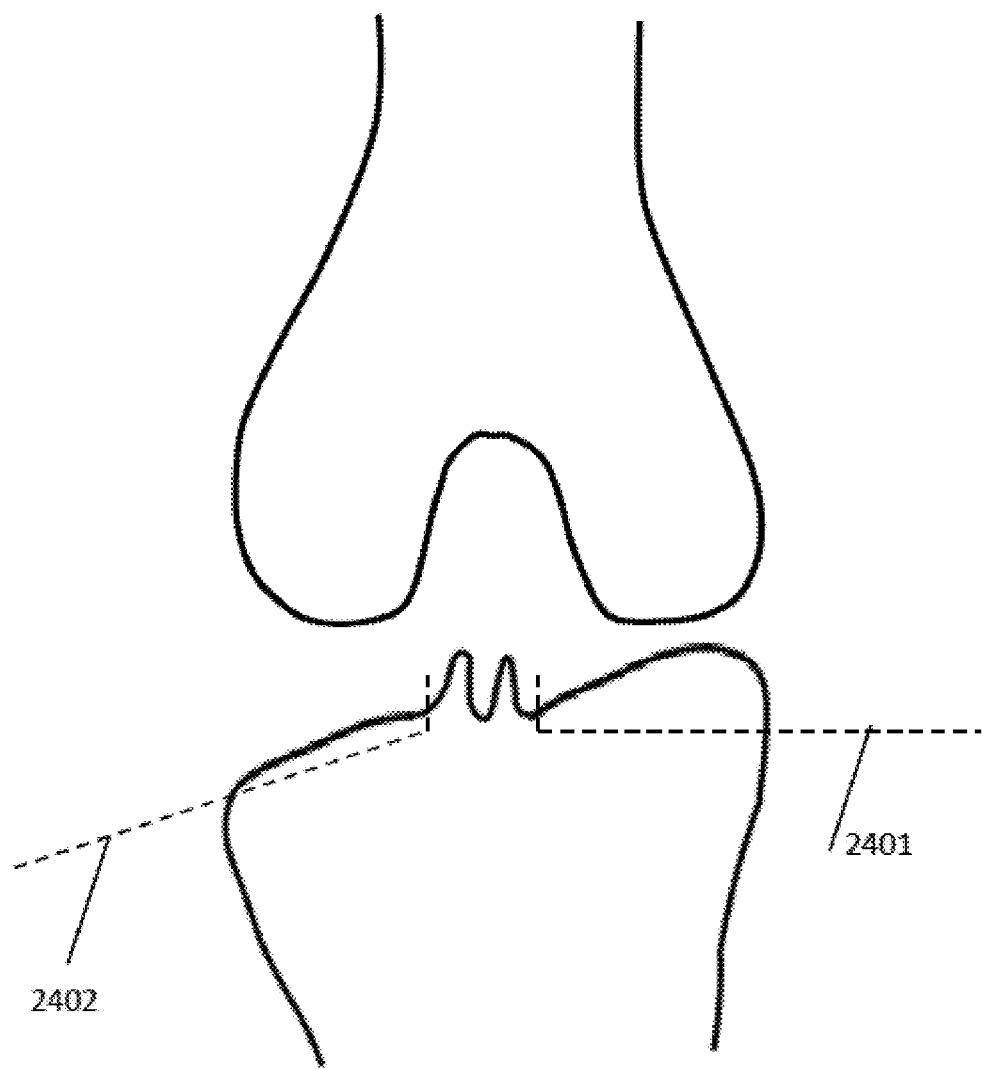
FIG. 24 depicts an exemplary knee joint with tibial cuts planned to differing levels and depths.
Figure 25:
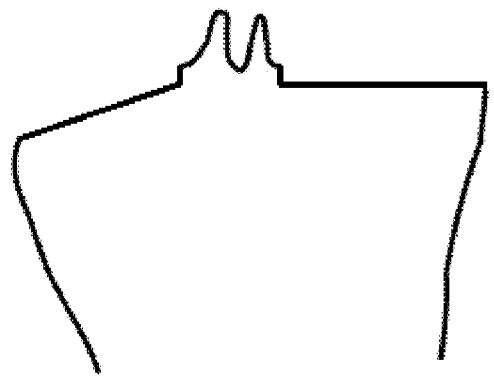
FIG. 25 depicts the knee joint of FIG. 24 in which a medial tibial section has been resected using a substantially horizontal cut and a lateral tibial section has been resected at a relatively steep angle.
Figure 26:
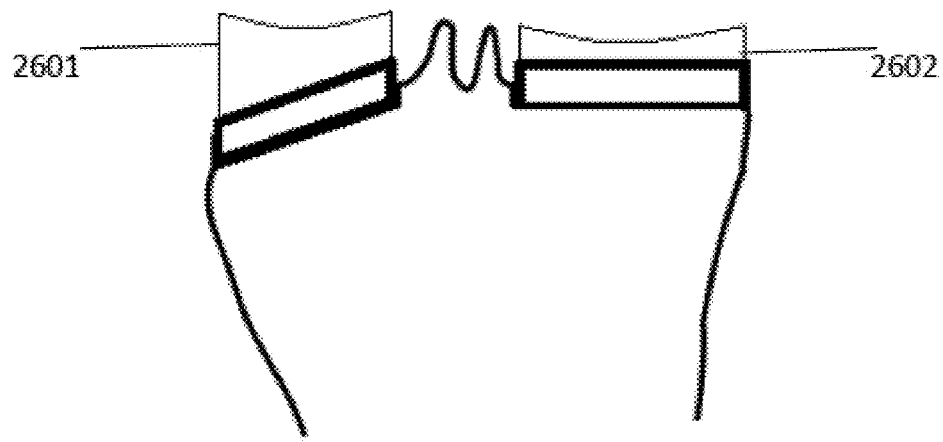
FIG. 26 depicts the tibia of FIG. 25, wherein a substantially thicker lateral insert than medial insert has been employed to create a desired resulting angulation.

In at least one alternative embodiment, various features of guide tools and surgical methods described herein can be used in conjunction with a wide variety of tibial trays, wedges and/or tibial inserts to accommodate the correction and/or reduction of extremely high varus and/or valgus angles in a given patient's anatomy. In such embodiments, a surgeon may choose to resect the medial and lateral portions of the tibia to differing levels and/or depths, as shown in FIG. 24, in which a medial tibial section has been resected using a substantially horizontal cut 2401, and a lateral tibial section has been resected at a relatively steep angle, desirably removing a minimal amount of bone from the lateral side (see FIG. 25). After resection and creation of the respective tibial cut planes, the surgeon can choose to employ various combinations of tibial trays (e.g., separate medial and lateral trays) and/or inserts (e.g., dual inserts) to desirably create and/or replicate medial and lateral tibial condylar surfaces that improve and/or correct the varus and/or valgus angles of one or both of the patient's knee joints. In the embodiment shown in FIG. 26, a substantially thicker lateral insert 2601 (as compared to the thickness of the medial insert 2602) has been employed to create a desired resulting angulation for the knee implant. In one alternative embodiment, a single tibial tray may be used with a single or multiple tibial cuts, with a one or two piece insert having differing thickness on each of the medial/lateral portions in a similar manner.

In addition, valgus deformities may lead to patients with deformed or hypoplastic lateral condyles. In fact, hypoplastic lateral condyles may be present in 20% of patients that require knee replacement. An implant or tibial guide assemblies or other tools may be engineered from patient-specific data to address this deformity, by correcting or optimizing the lateral condyle, can include one or more expanded curvatures in one or more locations on the lateral condyle, relative to the patient's corresponding uncut medial or lateral condyle. For example, an implant may be engineered to include additional material on the outer, joint-facing surface of the implant component's lateral condyle. The expanded curvature(s) and/or material on the outside of the condyle can be used to design a material savings on the inside of the corresponding section of the implant component, for example, by maintaining a minimum material/implant thickness from the outside (joint-facing surface) to the inside (bone-facing surface) of the implant component.

In this way, by adding material to the external contour of the implant component and maintaining a minimum material thickness of the implant component, bone preservation can be maximized. Specifically, with more material on the joint-facing surface of the implant and less material on the inner, bone-facing surface of the implant, the resection cuts are made closer to the surface of the bone. Accordingly, this approach uses the patient-adapted design of the implant component to both correct a condyle shape abnormality, such as a lateral condyle abnormality, such as hypoplasia, and to maximize bone preservation. In another embodiment, the deformity may be corrected by tailoring the tibial resection guide assemblies to have a unique medial and lateral assembly that will correct the angles. For example, the lateral condyle tibial resection guide may require smaller/lesser resection depth cut, different varus/valgus angle, or posterior/anterior angle than the medial tibial resection guide. Other tools and methods may be similarly designed to correct the deformity.

In an alternative embodiment, the tibial guide assembly, the joint implants, and other tools may be preoperatively designed and/or selected to correct the misalignment and/or obtain a proper mechanical alignment of a patient's limb. For example, based on the difference between the patient's misalignment and the proper mechanical axis, a knee implant and implant procedure can be designed and/or selected preoperatively to include implant and/or resection dimensions that substantially realign the patient's limb to correct or improve a patient's alignment deformity. In addition, the process can include selecting and/or designing one or more surgical tools (e.g., guide tools or cutting jigs) to direct the clinician in resectioning the patient's bone in accordance with the preoperatively designed and/or selected resection dimensions.

In certain embodiments, the degree of deformity correction that is necessary to establish a desired limb alignment is calculated based on information from the alignment of a virtual model of a patient's limb. The virtual model can be generated from patient-specific data, such 2D and/or 3D imaging data of the patient's limb. The deformity correction can correct varus or valgus alignment or antecurvatum or recurvatum alignment. In a preferred embodiment, the desired deformity correction returns the leg to normal alignment, for example, a zero degree biomechanical axis in the coronal plane and absence of genu antecurvatum and recurvatum in the sagittal plane.

The preoperatively designed and/or selected implant or implant component, resection dimension(s), and/or cutting guides, templates or cutting jig(s) can be employed to correct a patient's alignment deformity in a single plane, for example, in the coronal plane or in the sagittal plane, in multiple planes, for example, in the coronal and sagittal planes, and/or in three dimensions. For example, where a virtual model of a patient's misaligned lower limb is used to virtually correct the limb, a deformity correction can be achieved by designing and/or selecting one or more of a resection dimension, an implant component thickness, and an implant component surface curvature that adjusts the mechanical axis or axes into alignment in one or more planes. In various embodiments, a lower limb misalignment can be corrected in a knee replacement by designing or selecting one or more of a femoral resection dimension, a femoral implant component thickness, a femoral implant component surface curvature, a tibial resection dimension, a tibial implant component thickness, a tibial implant component insert thickness, and a tibial implant component surface curvature (or various combinations thereof) to adjust the femoral mechanical axis and tibial mechanical axis into alignment in the coronal plane.

Figure 27:
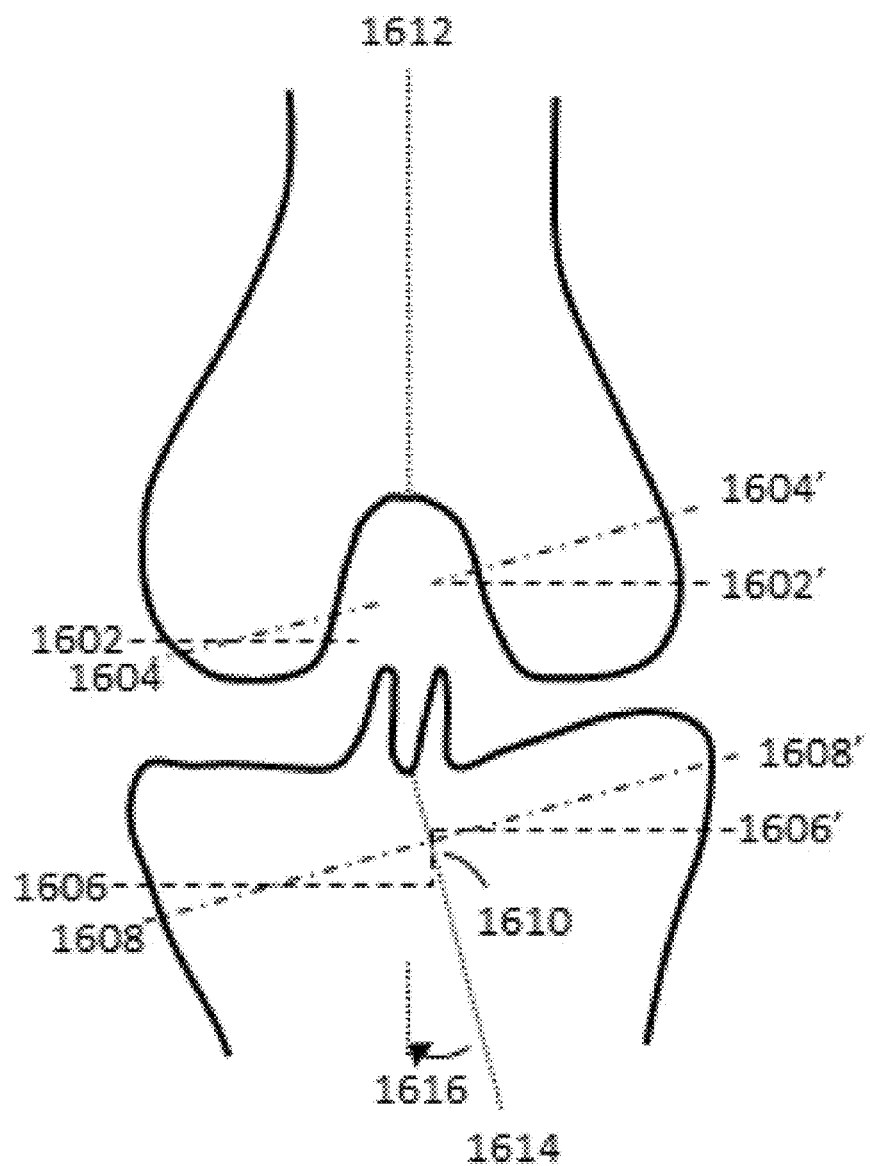
FIG. 27 illustrates a coronal plane of the knee with exemplary resection cuts that can be used to correct lower limb alignment in a knee replacement.

FIG. 27 illustrates a coronal plane of the knee with exemplary resection cuts that can be used to correct lower limb alignment in a knee replacement. As shown in the figure, the selected and/or designed resection cuts can include different cuts on different portions of a patient's biological structure. For example, resection cut facets on medial and lateral femoral condyles can be non-coplanar and parallel 1602, 1602', angled 1604, 1604', or non-coplanar and non-parallel, for example, cuts 1602 and 1604' or cuts 1602' and 1604. Similar, resection cut facets on medial and lateral portions of the tibia can be non-coplanar and parallel 1606, 1606', angled and parallel 1608, 1608', or non-coplanar and non-parallel, for example, cuts 1606 and 1608' or cuts 1606' and 1608. Non-coplanar facets of resection cuts can include a step-cut 1610 to connect the non-coplanar resection facet surfaces. Selected and/or designed resection dimensions can be achieved using one or more selected and/or designed guide tools (e.g., cutting jigs) that guide resectioning (e.g., guide cutting tools) of the patient's biological structure to yield the predetermined resection surface dimensions (e.g., resection surface(s), angles, and/or orientation(s)). In certain embodiments, the bone-facing surfaces of the implant components can be designed to include one or more features (e.g., bone cut surface areas, perimeters, angles, and/or orientations) that substantially match one or more of the resection cut or cut facets that were predetermined to enhance the patient's alignment. As shown in FIG. 27, certain combinations of resection cuts can aid in bringing the femoral mechanical axis 1612 and tibial mechanical axis 1614 into alignment 1616.

Figure 28:
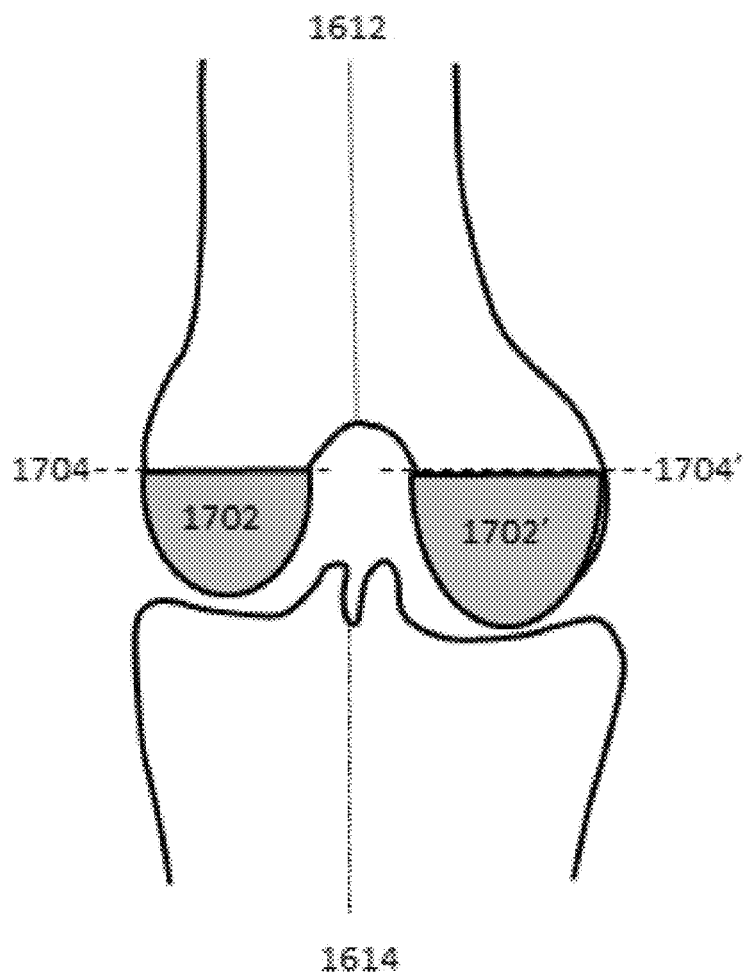
FIG. 28 depicts a coronal plane of a knee shown with femoral implant medial and lateral condyles having different thicknesses to help to correct limb alignment.

Alternatively, or in addition, certain implant features, such as different implant thicknesses and/or surface curvatures across two different sides of the plane in which the mechanical axes 1612, 1614 are misaligned also can aid correcting limb alignment. For example, FIG. 28 depicts a coronal plane of the knee shown with femoral implant medial and lateral condyles 1702, 1702' having different thicknesses to help to correct limb alignment. These features can be used in combination with any of the resection cut 1704, 1704' described above and/or in combination with different thicknesses on the corresponding portions of the tibial component. As described more fully below, independent tibial implant components and/or independent tibial inserts on medial and lateral sides of the tibial implant component can be used enhance alignment at a patient's knee joint. An implant component can include constant yet different thicknesses in two or more portions of the implant (e.g., a constant medial condyle thickness different from a constant lateral condyle thickness), a gradually increasing thickness across the implant or a portion of the implant, or a combination of constant and gradually increasing thicknesses.

FIG. 29 illustrates a virtual model of a patient's limb that is misaligned in the sagittal plane, for example, a genu antecurvatum deformity, and the virtually corrected limb. More particularly, FIG. 29 shows the misaligned limb in the sagittal plane 3001 and the coronal plane 3002, and the corrected limb in sagittal plane 3003 and coronal plane 3004. The deformity correction can be achieved using a similar design approach as described above for a coronal plane deformity. However, the selection and/or design of one or more femoral resection dimensions, femoral implant component thicknesses, femoral implant component surface curvatures, tibial resection dimensions, tibial implant component thicknesses, tibial implant component insert thicknesses, and/or tibial implant component surface curvatures can be used to adjust the femoral mechanical axis and tibial mechanical axis into alignment in the sagittal plane (e.g., by altering corresponding features across the sagittal plane, for example, by altering anterior features relative to corresponding posterior features). Alignment deformities in both the coronal and sagittal planes, or in multiple planes about the mechanical axes, can be addressed by designing and/or selecting one or more resection dimensions, one or more implant component thicknesses, and/or one or more implant component surface curvatures.

In certain embodiments, an implant component that is preoperatively designed and/or selected to correct a patient's alignment also can be designed or selected to include additional patient-specific or patient-engineered features. For example, the bone-facing surface of an implant or implant component can be designed and/or selected to substantially negatively-match the resected bone surface. If resection dimensions are angled, for example, in the coronal plane and/or in the sagittal plane, various features of the implant component, for example, the component bone-facing surface, can be designed and/or selected based on an angled orientation into the joint rather than on a perpendicular orientation. For example, the perimeter of the tibial implant or implant component that substantially positively-matches the perimeter of the patient's cut tibial bone has a different shape depending on the angle of the cut. Similarly, with a femoral implant component, the depth or angle of the distal condyle resection on the medial and/or lateral condyle can be designed and/or selected to correct a patient alignment deformity. However, in so doing, one or more of the implant or implant component condyle width, length, curvature, and angle of impact against the tibia can be altered. Accordingly in certain embodiments, one or more implant or implant component features, such as implant perimeter, condyle length, condyle width, curvature, and angle is designed and/or selected relative to a sloping and/or non-coplanar resection cut.

Figure 14:
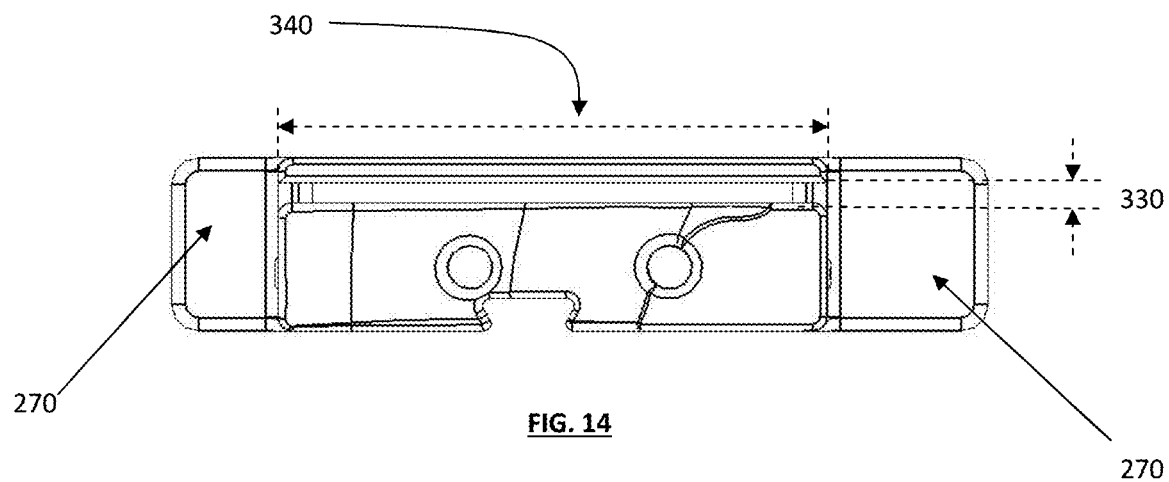
FIG. 14 depicts a back view of a "zero cut depth" guide box.

FIG. 14 depicts a back view of a tibial guide box. The back view shows a width 340 of the slot and a height 330 of the slot. The width of the guided slot 340 may also be specifically designed to control the width of the cut as required by the surgeon—it may be wider, it may be shorter or a specific cut shape. In various embodiments, the width of the preferred embodiment could substantially match the width of the specific implant components that will be placed on the tibia. The height 330 of the guided slot will desirably determine the cut depth of the tibial plateau, with the angulation of the slot similarly controlling and/or influencing the angulation of the cut plane (in both medial/lateral angulation as well as anterior/posterior angulation). In various embodiments, the cut plane height and/or angulation(s) may be patient specific as determined by each patient's anatomy, or some or all cut plane features could be "dialed in" using an adjustable mechanism as seen in FIG. 13B.

Figure 15:
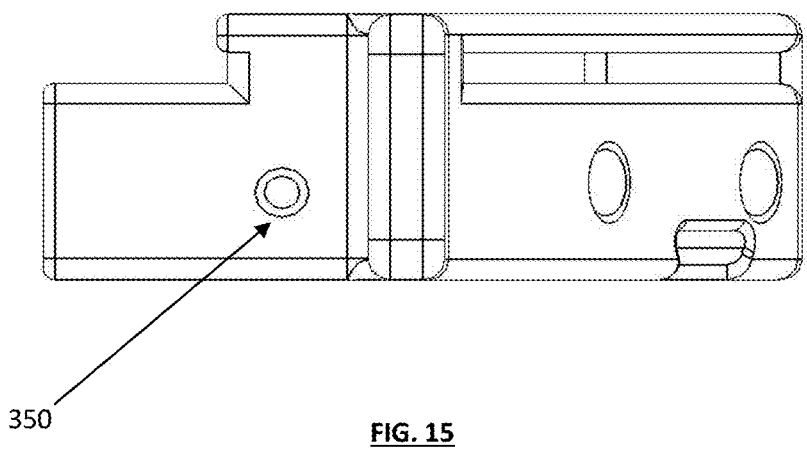
FIG. 15 depicts a side view of the guide box of FIG. 14.

FIG. 15 depicts a side view of a tibial guide box. The side view highlights the detent 350 which can used in various embodiments to lock into the detent receiver holes 230 (see FIG. 5). One or more of these detents can be placed on opposing sides of the box to ensure that an audible sound is heard (or other indication is provided) when locking the tibial guide box into the tibial guide housing.

Figure 16A:
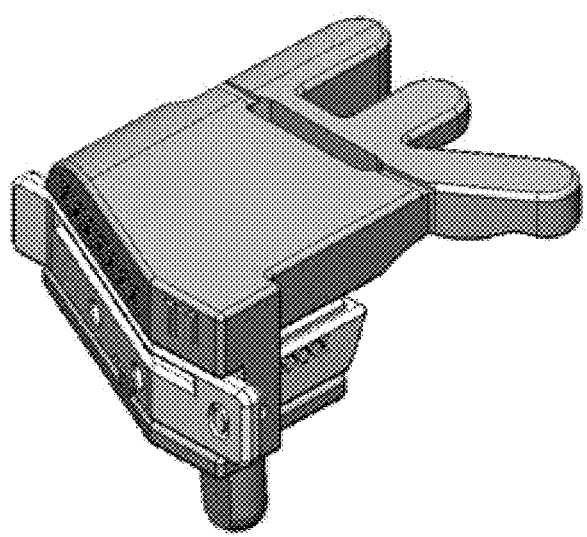
FIGS. 16A-16C depict isometric perspective, front plan, and back views of one embodiment of an assembled tibial guide assembly.
Figure 16B:
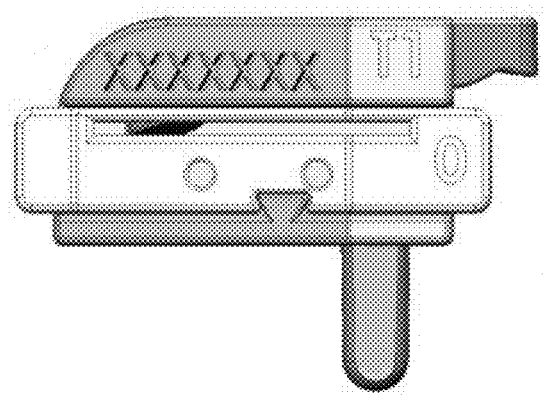
Figure 16C:
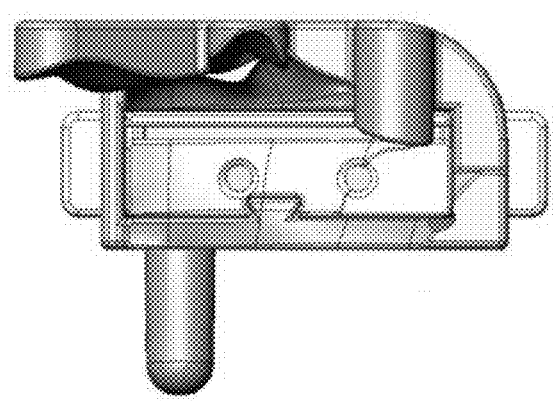

FIGS. 16A-16C depict an isometric view, a front view, and a back view of the tibial guide assembly, respectively. These shaded views show how an exemplary tibial guide box can fit within a corresponding tibial guide housing.

Improved Methods of Using a Tibial Guide Assembly

One preferred embodiment of the various teachings herein includes providing an apparatus and method for preparing the tibia for a tibial implant that significantly reduces the number of parts and component tools required to resect and prepare a tibial plateau, and desirably reduces the number of steps typically required in such a procedure. One of the many advantages of various embodiments described herein is that the assembly and associated components are modular, which allows the tibial housing to remain attached on the tibia, while multiple tibial guide boxes with varying cut depth dimensions, varus/valgus angles, and posterior/anterior cut angles can be utilized by the surgeon to make additional cuts and/or increase or modify the depth of cuts.

Figure 17A:
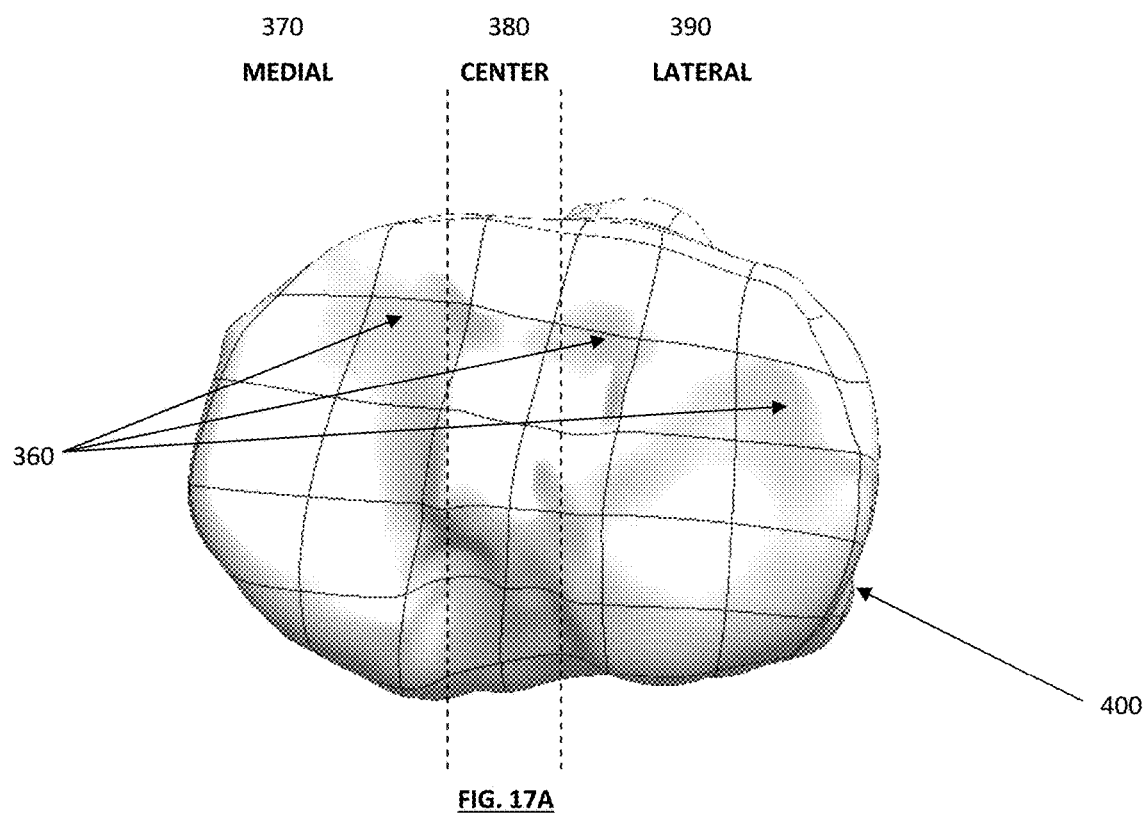
FIGS. 17A & 17B depict a top plan view and an anterior view of a patient's tibia remodeled by a computer system.

FIG. 17A depicts a top view of an uncut patient tibia 400 that has been modeled using a computer system. In this embodiment, there are three potential planes that the surgeon will be considering, which are the medial 370, the center 380 and the lateral 390 planes. Each of these planes has varying bone morphology that is shown by the articular ridges 360, and each plane may require a tibial guide assembly that attaches to the bone using the natural conforming bone anatomy adjacent thereto. The natural placement and positioning of an implant using the natural conforming bone anatomy will desirably provide the surgeon with a more secure tool to prepare and cut the tibial plateau.

Figure 17B:
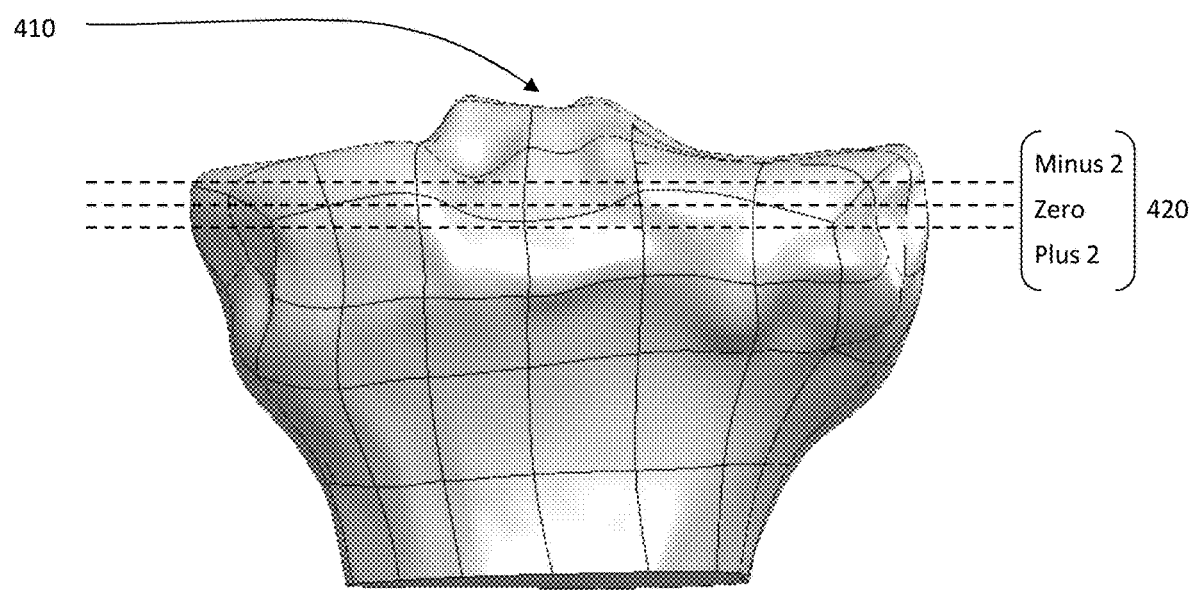

FIG. 17B shows an anterior view of a patient's uncut tibia and the medial and lateral intercondylar tubercle 410. This figure highlights the complex anatomy of a tibia and the varying exemplary cut planes 420 that a surgeon may desire in creating one or more desired cut planes to accept a tibial implant. The varying cut planes 420 show that the surgeon has already predetermined the cut depth, the varus/valgus angle, and the posterior/anterior angles that he or she wishes to make to prepare the tibia. However, once the surgeon has made one or more surgical access incisions and is able to directly visualize and/or observe the knee anatomy and the preparation required to cut the knee, the surgeon has the flexibility to adjust the predetermined cuts by using varying modular guide cut boxes with different cut depths and/or angles. For example, in one embodiment, if the surgeon wishes to cut less bone than originally predetermined, then the surgeon may choose the "Minus 2" tibial guide box instead of the "zero" guide box. This will allow the surgeon to cut less bone than what was originally predetermined.

Figure 18:
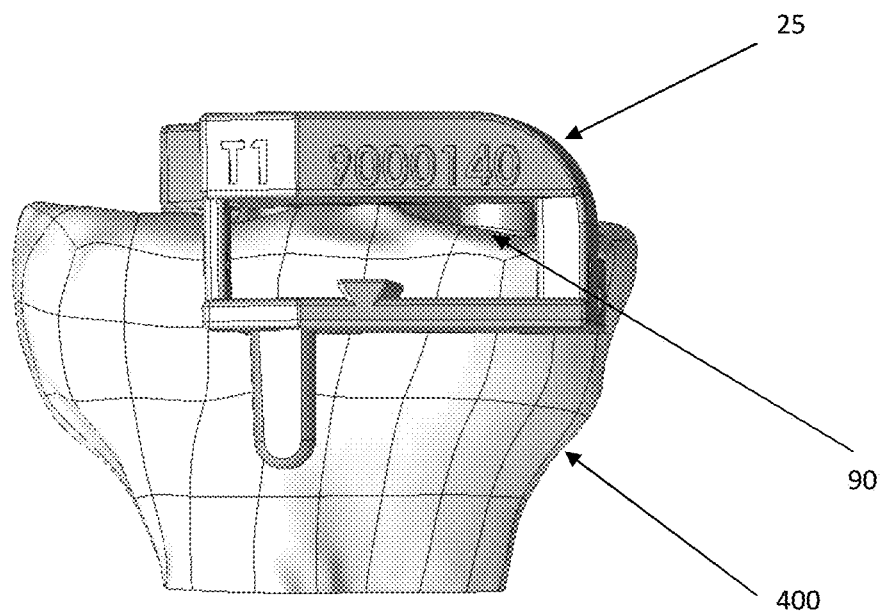
FIG. 18 depicts an anterior view of a tibial guide housing positioned on a medial side of a tibia.
Figure 19:
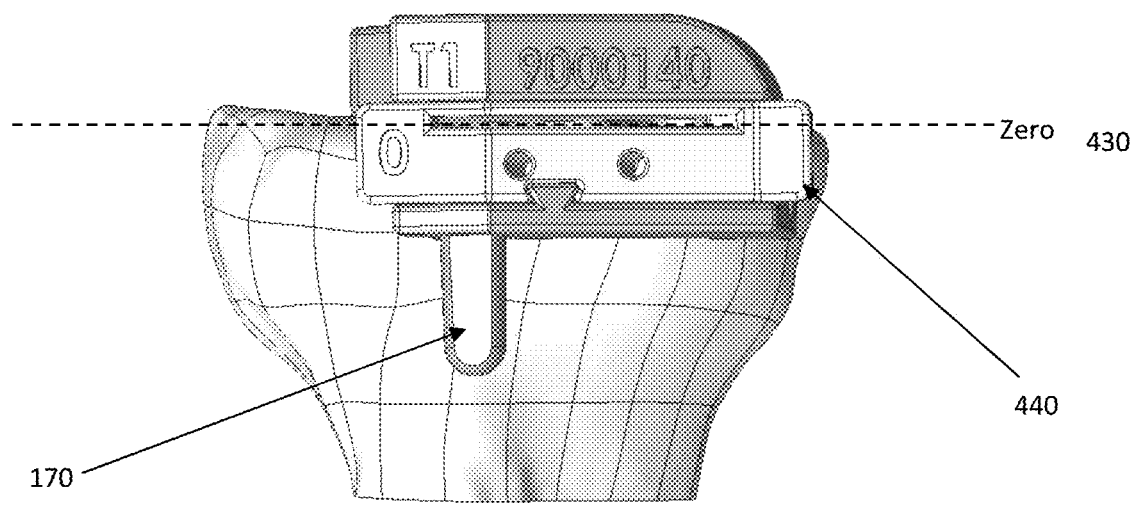
FIG. 19 depicts an anterior view of the tibial guide assembly and tibia of FIG. 18, with a "zero" tibial guide box inserted into the tibial guide housing.

FIG. 18 depicts an anterior view of a tibial guide housing 25 positioned on the medial side of the tibia 400 and showing the reference arms with a patient specific contact surface 90 conforming to the natural anatomy of the bone; the resection guide is aligned primarily to match natural landmarks of the articular surface or other features of the tibial plateau. Once a desired natural conforming position is found, the surgeon may score the articular surface to reach the subchondral bone to ensure proper positioning and placement, if desired. After the position has been determined, the surgeon may choose to determine the patient's mechanical axis with reference to their anatomical axis with an alignment rod or equivalent systems. For example, an alignment rod may be attached to a tibia guide housing 170 as shown in FIG. 19 and can extend to the patient's ankle to be parallel to the tibia's mechanical axis. The alignment rod system may be designed to be telescoped between its two connection points, which assists with the alignment of the patient's mechanical axis and provides preferred positioning that may be adjustable. The use of the alignment rod may, in various embodiments, provide the surgeon with an additional confirmation that the housing 170 is aligned with the correct patient-specific anatomy.

Figure 20:
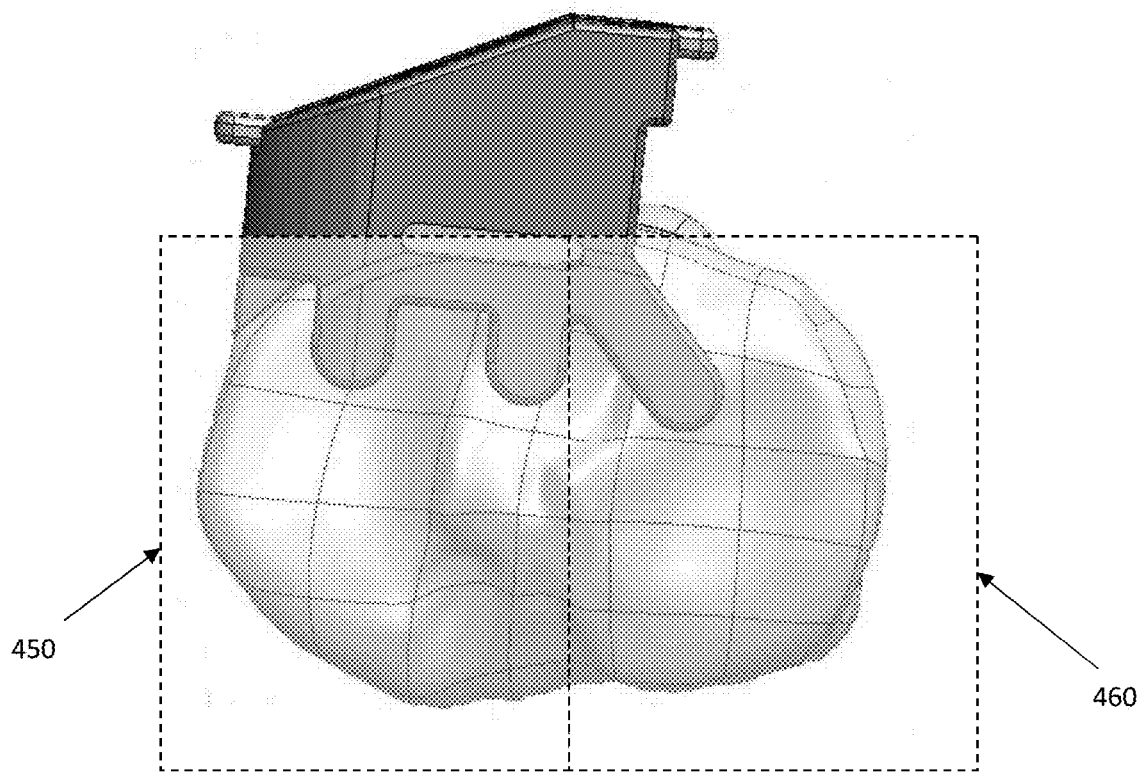
FIG. 20 depicts a top plan view of a tibial guide assembly, with exemplary medial and lateral cut planes.
Figure 21:
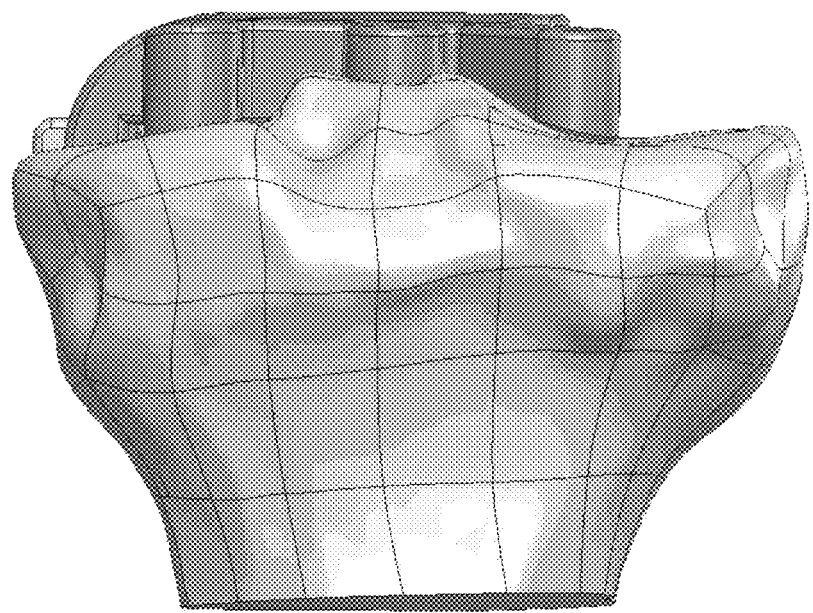
FIG. 21 depicts a posterior view of a tibial guide assembly positioned on a medial side of a tibia.

Once the alignment system is positioned, the tibial guide housing may be attached to the tibia using known methods and tools available in the OR, or provided in an instrument kit; and such attachment may include securement using a pin arrangement, e.g., by fitting one or more pins through appropriate openings in the tibial guide box (see FIG. 6) and/or the tibial guide housing. In various embodiments, after attaching the tibial guide housing to the anterior surface of the bone, a predetermined or adjusted tibial guide box may be inserted into the tibial guide housing. A reciprocating saw or similar cutting device can be fitted through a cutting guide slot in the tibial guide box and reciprocated or otherwise manipulated or employed to cut across the medial side 450 (see FIG. 20) tibial plateau with a predetermined or adjusted cutting plane 430. If the surgeon is satisfied with the cut, the entire tibial guide assembly may be removed and, if desired, the guide pins may be left in place and the steps may be repeated for the lateral side of the tibia using another lateral side tibial guide assembly. FIG. 20 depicts the top view of the tibial guide assembly and exemplary medial 450 and lateral 460 cut planes.

Figure 22:
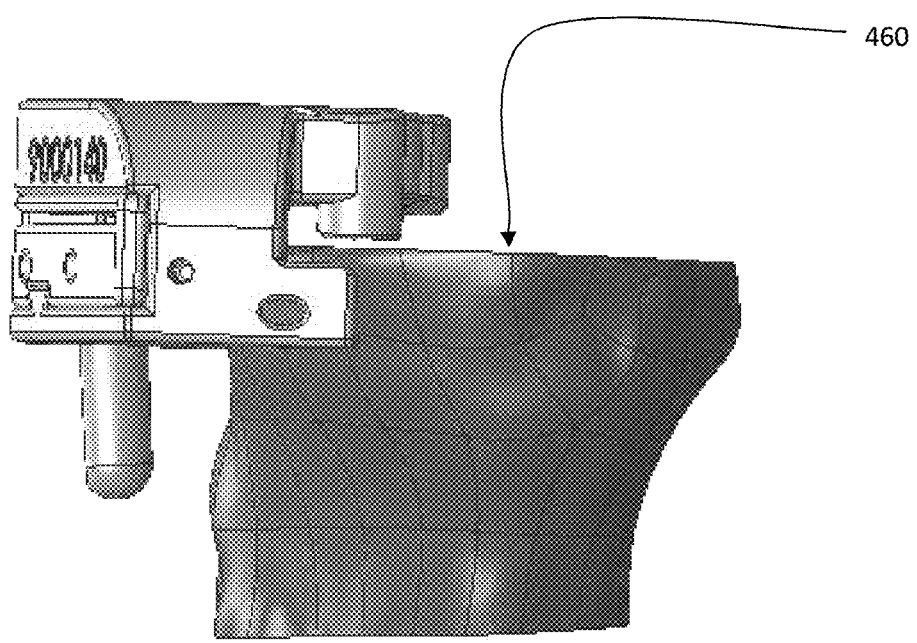
FIG. 22 depicts a side view of a tibial guide assembly, with both medial and lateral sides of a tibia resected.

FIG. 22 depicts a side view of a tibial guide assembly after both medial 450 and lateral 460 sides of the tibia have been resected; this figure highlights the uniformity of the entire cut tibial surface 460 when using the tibial guide assembly and captured/guided cut boxes. In various alternative embodiments, the medial and lateral cut planes may not be parallel, offset, and/or coplanar. At this time, the surgeon can remove the tibial guide assembly leaving the positioning pins for both the medial and lateral cuts in place to conduct a trialing and fixation of the knee prosthesis. The trialing may involve fitting the prosthesis components to the prepared surfaces and checking the patient's range of motion, alignment, and the ligament stability that will approximate the range of motion of a natural knee. In at least one exemplary embodiment, the proximal tibial end can preferably be first fitted with a variety of templates and measuring tools and be followed by fitting the femur portion of the prosthesis to the prepared distal femur end.

Figure 23:
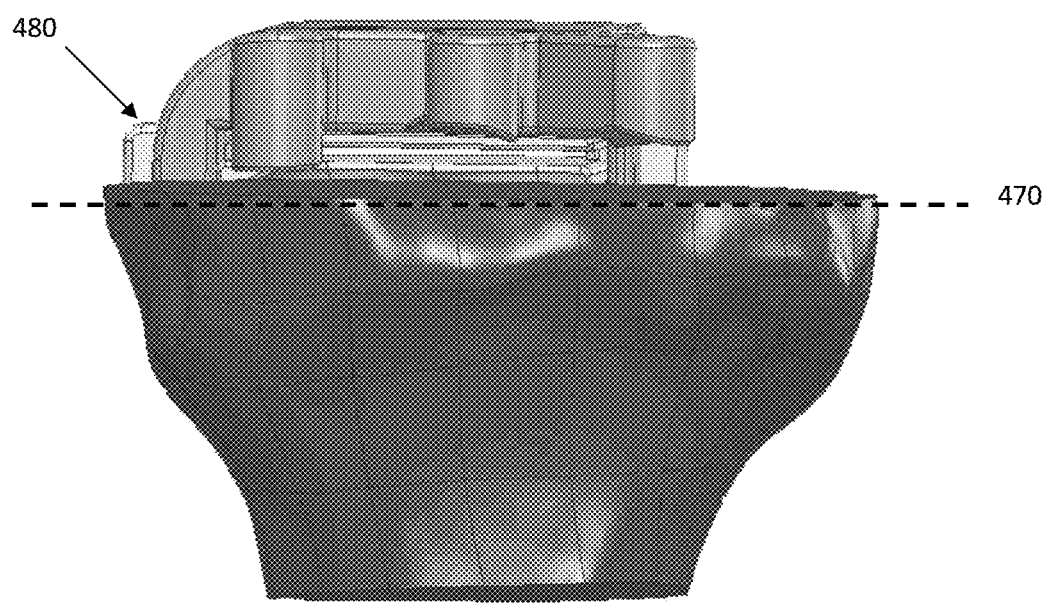
FIG. 23 depicts a posterior view of the tibial guide assembly with an optional cut plane.

If various trialing steps do not optimally fit the trial implant prosthesis, additional cuts on the tibia may be made. For example, if the knee is tight in extension and flexion, the tibia may be further resected as necessary using the tibial guide assembly and adjusting the tibial guide boxes 480 (in FIG. 23) to preferred cut depth and angles. If the knee is tight in extension and balanced in flexion, the distal femur may be cut. Lastly, if the knee is tight in flexion and balanced in extension, it is possible that the surgeon may choose a tibial guide cut box to add posterior/anterior slope to the already cut tibial surface. However, many other combinations may be found to optimally adjust the cut depth 470 of the tibia resected surface using the guide boxes and combinations of guide boxes with varying dimensions or angles.

Once the proper alignment and balancing of the trial implants have been performed, the surgeon may secure the actual knee joint components and patella prosthesis to the patella. The result can be tested and thereafter the incision into the knee can be appropriately closed and dressed.

What is claimed is:

1. A system for preparing a tibial plateau of a tibia of a patient, the system comprising:
   a tibial guide housing, the tibial guide housing comprising:

a top side generally opposite a bottom side a front side generally opposite a back side, and a medial side generally opposite a lateral side;

a first reference arm having a patient-specific contact surface configured to conform to a first tibial surface, the first tibial surface being a first portion of a superior surface of the tibia;

a second reference arm having a patient-specific contact surface configured to conform to a second tibial surface, the second tibial surface being a second portion of the superior surface of the tibia, wherein the back side includes a patient-specific contact surface configured to conform to a third tibial surface, the third tibial surface being a portion of an anterior surface of the tibia, wherein the patient-specific contact surface of the back side has a medial-most edge and a lateral-most edge;

wherein the tibial guide housing defines a void in at least a portion of the top side, the void sized and positioned such that when the tibial guide housing is positioned on the tibia and the patient-specific contact surfaces of each of the first reference arm, the second reference arm, and the back side are in conforming engagement with the first, second, and third tibial surfaces, respectively, a surgeon is able to view a portion of a peripheral edge of the anterior surface of the tibia, the portion of the peripheral edge of the anterior surface of the tibia having a medial-lateral position disposed between the medial-most edge and the lateral-most edge of the patient-specific surface of the back side; and one or more tibial cutting guide boxes, each of the one or more tibial cutting guide boxes comprising:

a guide aperture configured to accommodate a surgical cutting tool and guide the cutting tool along a cutting plane having a predetermined cut depth and angle; and at least one pin hole configured to accommodate a pin passing into the tibia, wherein at least one of the one or more tibial cutting guide boxes is configured for releasable securement within the tibial guide housing.

2. The system of claim 1, wherein the void comprises a viewing window configured to permit viewing of the portion of the peripheral edge of the anterior surface of the tibia from the top side of the tibial guide housing during positioning of the tibial guide housing on the tibia.

3. The system of claim 1, including at least two tibial cutting guide boxes, wherein each of the at least two tibial cutting guide boxes has a different cut depth.

4. The system of claim 3, wherein each of the at least two tibial cutting guide boxes are configured for releasable securement within the tibial guide housing.

5. The system of claim 1, wherein the patient-specific contact surface of each reference arm is configured to engage an articular surface of the tibial.

6. The system of claim 1, wherein the patient-specific contact surface of each reference arm is configured to engage subchondral bone surface.

7. The system of claim 1, wherein the top side includes a patient-specific alignment indicator configured to provide visual assistance for alignment of the tibial guide housing with respect to the tibia.

8. The system of claim 7, wherein the alignment indicator comprises one or more channels formed in the top surface of the tibial guide housing.

9. The system of claim 7, wherein the alignment indicator is positioned and shaped based, at least in part, on patient-specific information to substantially match a portion of a perimeter of the tibia when the tibial guide housing is positioned on the tibia in a predetermined alignment.

10. The system of claim 1, further comprising an alignment leg, the alignment leg configured for attachment to a tibial alignment rod.

11. The system of claim 1, wherein the tibial guide housing further comprises a third reference arm having a patient-specific contact surface configured to conform to a fourth tibial surface.

12. A method of preparing a tibial plateau of a tibia of a knee joint of a patient for implantation of at least one prosthesis, the method comprising:

providing a tibial guide housing, the tibial guide housing including:

a top side generally opposite a bottom side a front side generally opposite a back side, and a medial side generally opposite a lateral side;

a first reference arm having a patient-specific contact surface configured to conform to a first tibial surface, the first tibial surface being a first portion of a superior surface of the tibia;

a second reference arm having a patient-specific contact surface configured to conform to a second tibial surface, the second tibial surface being a second portion of the superior surface of the tibia, wherein the back side includes a patient-specific contact surface configured to conform to a third tibial surface, the third tibial surface being a portion of an anterior surface of the tibia, wherein the patient-specific contact surface of the back side has a medial-most edge and a lateral-most edge;

wherein the tibial guide housing defines a void in at least a portion of the top side, the void sized and positioned such that when the tibial guide housing is positioned on the tibia and the patient-specific contact surfaces of each of the first reference arm, the second reference arm, and the back side are in conforming engagement with the first, second, and third tibial surfaces, respectively, a surgeon is able to view a portion of a peripheral edge of the anterior surface of the tibia, the portion of the peripheral edge of the anterior surface of the tibia having a medial-lateral position disposed between the medial-most edge and the lateral-most edge of the patient-specific surface of the back side;

providing a first tibial cutting guide box, the first tibial cutting guide box including:

a guide aperture configured to accommodate a surgical cutting tool and guide the cutting tool along a cutting plane having a predetermined cut depth and angle; and at least one pin hole configured to accommodate a pin passing into the tibia;

releasably securing the first tibial cutting guide box within an opening of the tibial guide housing;

positioning the tibial guide housing on the tibia such that each of the patient-specific contact surfaces of the tibial guide housing achieves a conforming fit with the tibia; and inserting a cutting device through the guide aperture and cutting a portion of the tibia along the cutting plane.

13. The method of claim 12, further comprising removing the first tibial cutting guide box from the tibial guide housing.

14. The method of claim 12, further comprising selecting the first tibial cutting guide box from a plurality of tibial cutting guide boxes, each including a guide aperture having a different predetermined cut depth.

15. The method of claim 12, further comprising:
    positioning a trial prosthesis component on a cut surface of the tibia; and
    checking a state of the knee joint, wherein the state of the knee joint is selected from the group consisting of ligament stability of the knee joint, range of motion of the knee joint, alignment of the knee joint, and combinations thereof.

16. The method of claim 15, further comprising:
    selecting a second tibial cutting guide box from a plurality of tibial cutting guide boxes, each including a guide aperture having a different predetermined cut depth, based, at least in part, on the checking a state of the knee joint; and
releasably securing the second tibial cutting guide box within the opening of the tibial guide housing.

\* \* \* \* \*